(12) United States Patent
Aljefri

(10) Patent No.: US 11,781,105 B2
(45) Date of Patent: Oct. 10, 2023

(54) METHOD, SYSTEM, AND APPARATUS USING CENTRIFUGATION TO ACCUMULATE AND COLLECT BIOLOGICAL SAMPLES

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Ahmad Mohammed Shikan Aljefri, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 548 days.

(21) Appl. No.: 16/894,246

(22) Filed: Jun. 5, 2020

(65) Prior Publication Data
US 2021/0380926 A1    Dec. 9, 2021

(51) Int. Cl.
*C12M 1/00* (2006.01)
*C12M 1/12* (2006.01)
(Continued)

(52) U.S. Cl.
CPC ............ *C12M 45/05* (2013.01); *C12M 23/04* (2013.01); *C12M 23/38* (2013.01); *C12N 1/02* (2013.01); *C12Q 1/04* (2013.01)

(58) Field of Classification Search
CPC ...... C12M 45/05; C12M 23/04; C12M 23/38; C12M 23/02; C12M 25/14; C12M 33/10; C12N 1/02; C12Q 1/04
See application file for complete search history.

(56) References Cited

U.S. PATENT DOCUMENTS 3,623,958 A * 11/1971 Fitzgerald .............. C12M 23/50
                                                      435/243
3,660,243 A *  5/1972 Young .................... C12M 33/00
                                                      435/309.1
(Continued)

FOREIGN PATENT DOCUMENTS

JP       5853626 B2    2/2016
WO   2019/014541 A2    1/2019

OTHER PUBLICATIONS

Jaquith, Kevin - 96-Well plate dimensions [Standard microplate] Pub 2014, pp. 1-3 (Year: 2014).*
(Continued)

*Primary Examiner* — William H. Beisner
*Assistant Examiner* — Danielle B Henkel
(74) *Attorney, Agent, or Firm* — Oblon, McClelland, Maier & Neustadt, L.L.P.

(57) ABSTRACT

A system for quickly determining antibiotic sensitivity of a microorganism comprising a triangular-shaped plate and cover for culturing, recovering, and re-suspending recovered microbial colonies and a second triangular-shaped plate comprising a non-liquid medium cut with concentric trenches over which the re-suspended microbial colonies are distributed by centrifugation and contacted with antimicrobial strips or disks.

17 Claims, 11 Drawing Sheets

(51) Int. Cl.
*C12Q 1/04* (2006.01)
*C12N 1/02* (2006.01)

(56) References Cited

U.S. PATENT DOCUMENTS

| | | | | |
|---|---|---|---|---|
| 4,981,802 A * | 1/1991 | Wylie | .................... | C12M 23/48 |
| | | | | 435/286.3 |
| 5,141,718 A * | 8/1992 | Clark | .................... | C12M 23/12 |
| | | | | 435/297.5 |
| 8,753,875 B2 | 6/2014 | Frimodt-Moller | | |
| 2006/0019377 A1* | 1/2006 | Cattadoris | .............. | C12M 23/00 |
| | | | | 435/304.3 |
| 2006/0135337 A1* | 6/2006 | Kerrod | ................. | G01N 1/2813 |
| | | | | 494/15 |
| 2007/0031963 A1* | 2/2007 | Chang | .................... | C12M 23/08 |
| | | | | 435/304.2 |
| 2007/0202564 A1* | 8/2007 | Glasson | ................ | C12M 33/02 |
| | | | | 435/309.3 |
| 2008/0064090 A1* | 3/2008 | Whittlinger | ........... | B01L 3/5085 |
| | | | | 435/305.3 |
| 2009/0068696 A1* | 3/2009 | Frimodt-Moller | ..... | C12M 41/36 |
| | | | | 435/19 |
| 2010/0221768 A1* | 9/2010 | Akai | ...................... | C12M 23/10 |
| | | | | 435/29 |
| 2013/0115691 A1* | 5/2013 | Schryver | ................ | C12M 41/12 |
| | | | | 435/303.1 |
| 2013/0189671 A1* | 7/2013 | Hoh | ........................ | C12M 23/34 |
| | | | | 435/297.1 |
| 2016/0222335 A1* | 8/2016 | Akai | ...................... | C12M 41/36 |
| 2017/0067008 A1* | 3/2017 | Kiedrowski | ........... | C12M 23/22 |
| 2017/0145362 A1* | 5/2017 | Ito | .......................... | C12M 29/14 |
| 2020/0154698 A1* | 5/2020 | Takeuchi | ................. | C12M 1/14 |
| 2020/0199507 A1* | 6/2020 | Okon | ..................... | C12M 23/22 |
| 2021/0079329 A1* | 3/2021 | Souza | ..................... | C12M 23/38 |
| 2022/0238042 A1* | 7/2022 | Mokhtari | ............. | G09B 23/306 |

OTHER PUBLICATIONS

Nalge Nunc International ; Nunc Cell Culture Flasks, Thermo Scientific ; 2017 ; 2 Pages.

University of Maryland ; Nomogram for converting maximum relative centrifugal force (RCF, i.e., gh-force) to RPM ; Aug. 22, 2012 ; 1 Page.

* cited by examiner

METHOD, SYSTEM, AND APPARATUS USING CENTRIFUGATION TO ACCUMULATE AND COLLECT BIOLOGICAL SAMPLES

BACKGROUND OF THE INVENTION

Field of the Invention

The invention falls within the field of medical diagnostics. It involves a trianguloid plate microbial culturing and centrifuging system and a method for using the system to gather and accumulate biological samples thus simplifying and accelerating the detection of antibiotic sensitivity of a microbe.

Description of Related Art

Conventional antibiotic testing for bacteria is slow and time consuming. It often takes days to determine to whether, or to which antibiotic an infectious bacterium or other microorganism is sensitive. According, a patient is usually only empirically administered an antibiotic until antibiotic sensitivity results are available at which time a better selection of an antibiotic can be made.

Conventional antibiotic resistance testing typically involves the collection of a sample of a microbe, typically a body fluid sample from an infected patient, which is then subjected to series of laboratory procedures to determine the antibiotic sensitivity of the microbe. Once antibiotic sensitivity is determined a physician can rationally administer the most effective antibiotic to treat the patient's infection.

Conventional methods for determining antibiotic sensitivity include the broth dilution method and the disk diffusion method.

The broth dilution method involves subjecting the sample to a series of concentrations or serial dilutions of an antimicrobial agent in a culture broth. The lowest concentration at which growth or viability the isolate is completely inhibited, as evidenced by the absence of visible bacterial growth in the culture broth, is recorded as the minimal inhibitory concentration or MIC. The MIC is the minimum concentration of the antibiotic that will inhibit a particular microbial isolate. This method may compare the results obtained from a clinical isolate with those of a negative control not inoculated with a microbe and/or positive control, inoculated with a known microbe. Such a test may be validated when the positive control shows growth and the negative control shows no growth.

In the disk diffusion method a solid growth medium, usually Mueller-Hinton agar, is evenly seeded with the isolate of interest. Typically the isolate is dispersed or precultured in a broth medium, diluted to a standard concentration, for example, approximately 1 to $2 \times 10^8$ colony forming units per ml, and then evenly distributed over the gel (e.g., agar) or solid growth medium.

Once the microbe-seeded gel or solid medium plates have been prepared, one or more antibiotic impregnated disks or strips are applied to the surface of the gel or solid medium. The test antibiotics diffuse outward from the strips or disks, creating a gradient of antibiotic concentrations in the non-liquid, gel or solid medium such that the highest concentration is found close to the disk with decreasing concentrations further away from the disk.

After an overnight period of incubation, the microbial growth around each disk is observed. If the microbe in the test isolate is susceptible to a particular antibiotic, a clear area of "no growth" or zone of inhibition will be observed around that particular disk. The zone around an antibiotic disk that has no growth is referred to as the zone of inhibition since this approximates the minimum antibiotic concentration sufficient to prevent growth of the test isolate. This zone can be measured in mm and compared to a standard interpretation chart used to qualitatively categorize the microbe (or microorganism) in the isolate as a susceptible, intermediately susceptible, or resistant microbe.

Methods based on culturing microorganism microbe in a petri dish containing a solid medium, such as an agar-based medium or in Mueller-Hinton agar are time-consuming and delay the selection of an antibiotic effective to treat the patient's infection. For example, such methods generally require culture in a fluid medium, gram staining the cultured microbe, culture in a petri dish to collect microbial colonies, resuspension of the colonies at a proper optical density and followed by swabbing a sample of the suspension on Muller-Hinton agar along with antibiotic disks or strips to determine antibiotic sensitivity.

The delays caused by these steps increase the risk of an empirical selection of an ineffective antibiotic and progression of the infection, require a longer period of medical observation, and often a result in a prolonged stay in the hospital.

Moreover, many of the conventional steps involve open containers containing infectious bacteria and risk contamination of a sample with exogenous microbes or risk transmission of infectious microbes to laboratory workers doing the testing.

In view of the limitations of conventional methods for rapidly culturing microbes for antibiotic testing and in view of the prolonged time requires to acquire a result from conventional antibiotic testing methods, the inventor sought to develop a simple and quick method for culturing microbes and for determining microbial antibiotic sensitivity using a trianguloid dish system.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One aspect of the invention is a "centrifugation accumulated colonies triangular agar technology" or "CAC-TAT" system which is employed for rapid culturing, harvesting and collection of microbe colonies. This system comprises a triangular shaped culture plate shaped like a slice of pie that permits aggregation and collection of microbe colonies at its apex by centrifuging the plate, a growth medium for a microbe, a holder or adaptor to fit a triangular plate into a centrifuge and a centrifuge. It also comprises a type 1 cover having an injectable septum through which a microbial sample can be aseptically applied to medium in the trianguloid plate and optionally a type 2 cover to facilitate removal and collection of microbe colonies.

A related aspect is a method for using the CAC-TAT system to rapidly grow, harvest and collect by centrifugation microbial colonies. Once collected, the colonies can be resuspended in a suitable buffer for further use, for example, in a method for determining which antibiotics the microbes are sensitive to.

Another aspect of the invention involves a system for determining antibiotic sensitivity. This system comprises a triangular shaped culture plate shaped like a slice of pie that permits distribution of a suspension of by centrifuging the plate, a plate cover, a nonliquid growth medium, antibiotic strips or disks, a holder or adaptor to fit a triangular plate into a centrifuge and a centrifuge. In some embodiments, the medium is precut or cast concentric trenches and can have a type 1 cover with a septum. In other embodiments, the plate is fitted with a type 3 cover for producing concentric trenches which may also have an injectable septum or which can be replaced after trenching the non-liquid medium with a type 1 cover. This system distributes the aggregated and resuspended microbe colonies grown, detached, aggregated by centrifugation, and resuspended as described above.

Another aspect of the invention is a method for determining antibiotic sensitivity using the system disclosed herein. Once grown and aggregated microbe colonies are resuspended at a suitable concentration they are distributed by centrifugation over the several surface areas defined by trenches cut into the surface of the growth medium (see FIGS. 5 and 6). Typically, a sample of the resuspended microbe colonies is applied to the outermost area (Area 1) and then distributed by centrifuging the plate to produce a gradient of different concentrations of microbe in the remaining areas, such as Areas 2, 3, 4, and 5 shown in FIGS. 5 and 6. Antibiotic test strips or disks are then applied to the areas comprising the distributed microbes and zones of microbial inhibition are measured around the strips or disease after growth of the bacteria. The size of a zone of inhibition indicates the degree of sensitivity of the distributed microbe to that antibiotic in the strip or disk.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIG. 14B depicts container 178. FIG. 14C provides an exploded view of the embodiment of the system having drainage tip built into the cover (cover 2).

DETAILED DESCRIPTION OF THE INVENTION

One aspect of the invention is a "centrifugation accumulated colonies technology" or "CAC-TAT" system which is employed for rapid culturing, harvesting and collection of microbe colonies. This system comprises a triangular shaped culture plate shaped like, much like a slice of a pie that permits collection and aggregation of microbial colonies by centrifuging the plate and recovering aggregated microbial colonies at the apex of the trianguloid plate.

In this system, the trianguloid plate holds a culture medium for growing colonies of a microbe. The system has a type 1 cover (FIGS. 1 and 2) which covers the space containing the non-liquid culture medium, but which has an injectable septum through which a sample containing a microbe to be cultured can be aseptically applied to a predetermined position on the surface of the solid medium in the plate and from there spread over the surface of the medium, for example, by tipping the plate back-and-forth. After that the drops are further distributed to cover the whole plate by centrifugation the plates. Then the plate incubated at 37° C. to allow for the microbial growth.

Typically, the microbes grown on the medium represent a mixed flora in a clinical sample and are cultured for later use for evaluating their antibiotic sensitivity. The non-liquid medium may be a rich growth medium that supports the growth of different types of microbes or a selective medium that permits only the growth of particular types of microbes. In some embodiments, the aggregated microbe colonies may be used for other procedures requiring a suspension of microbes obtained or isolated from a clinical sample, for example, for further phenotypic (e.g., toxin expression, capsule type, etc.) or genetic characterization (e.g., Western blot analysis or DNA sequencing) or for cloning or comparison to microbes in other clinical samples. This culture system can grow the same types of microbes as grown in conventional broth culture, but the microbe colonies that it grows on medium appear faster and in a form which can be conveniently aggregated by soaking, rinsing and/or curettage and then centrifugation.

Once colonies appear on the surface of the medium in the plate they are prepared for removal by soaking, rinsing and/or curettage and then for collection by centrifuging the plates to collect the loosened or curettaged colonies at the apex of the triangular plate.

Figure 14A:
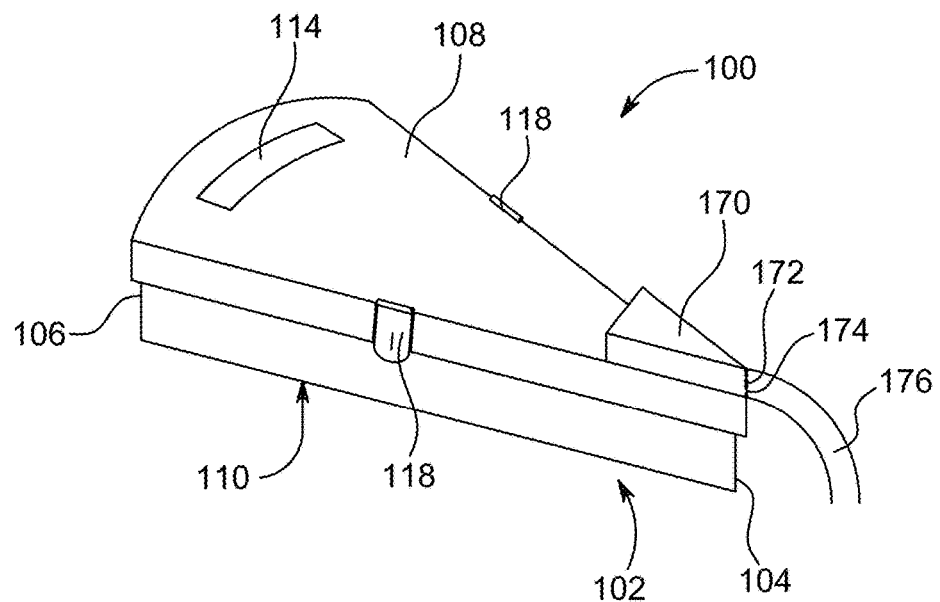
FIGS. 14A-14C illustrate an embodiment of the trianguloid culturing and centrifuging system 100 having a drainage tip at apical end 104. The drainage tip 170, drainage filter 172, opening at apical tip 174 and drainage pipe 176 are depicted at the apical end 104 of the system.
Figure 14B:
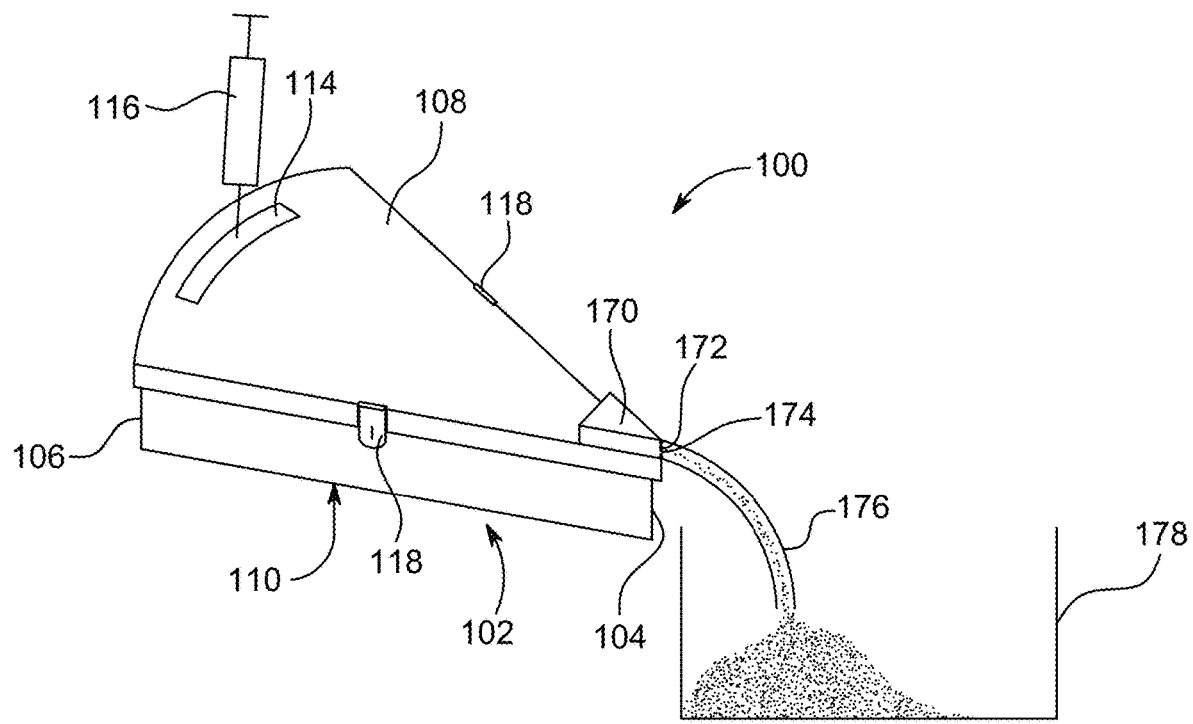
Figure 14C:
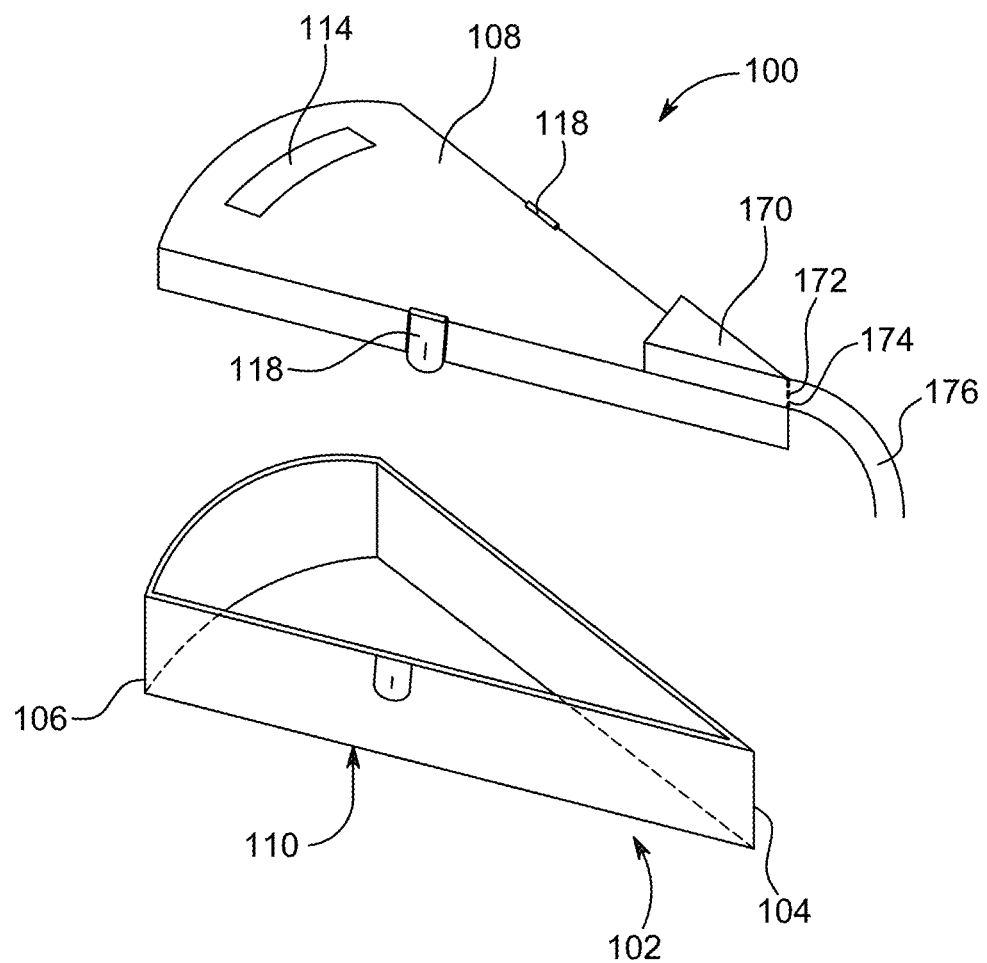

Once microbe colonies are grown and appear on the surface of the non-liquid medium in the trianguloid plate, they may be loosened by soaking or rinsing (e.g. in a saline solution) and/or curettaged to facilitate their collection at the apical tip of the plate by centrifugation. To facilitate removal and collection of the colonies, the type 1 plate cover which permitted aseptic injection of the clinical sample and protected the medium from contamination while the microbe colonies grew, may be replaced by a type 2 plate cover which has a drainage tip (FIGS. 14A-14C) and filter which facilitates removal and collection of the colonies grown on the medium.

In some embodiments, all the colonies grown on the medium are removed (for example, when a clinical sample contains substantially only one type of pathogenic microbe), in other embodiments colonies conforming to a particular phenotype (colony texture, color, texture or morphology) are selectively removed by soaking, rinsing and/or curettage prior to centrifugal collection of the loosened or removed colonies at the apical tip of the trianguloid plate.

After collection of the loosened or curettaged colonies and aggregation and collection by centrifuging the plate, the aggregated microbe colonies can be resuspended at a desired concentration or turbidity and used to determine antibiotic sensitivity of the microbe. A concentration of resuspended microbes may be selected by one skilled in the art to provide an appropriate gradient of microbes for testing antibiotic sensitivity of a particular microbe or for a particular antibiotic. In one embodiment, the microbes are re-suspended to a McFarland density concentration (turbidity) ranging from 0.5, 1, 2, 3 to 4, preferably about 0.5. The 0.5 McFarland turbidity standard provides an optical density comparable to the density of a bacterial suspension $1.5 \times 10^8$ colony forming units (CFU/ml). McFarland turbidity standards are commercially available.

Another aspect of the invention involves a system for determining antibiotic sensitivity. This system uses the aggregated and resuspended microbe colonies grown, detached, aggregated by centrifugation, and resuspended as described above. Once these aggregated microbes are resuspended at a suitable concentration they are distributed by centrifugation over the several surface areas (FIGS. 5 and 6), defined by trenches cut into the surface of the non-liquid growth medium. Typically, a sample of the resuspended microbe colonies is applied to the outermost area (Area 1) and then distributed by centrifuging the plate to produce a gradient of different concentrations of microbe in the remaining areas, such as Areas 2, 3, 4, and 5 shown in FIGS. 5 and 6.

In some embodiments, the growth medium in the plate is precast or precut with concentric trenches which define the surface areas, such as Areas 1-5, on the surface of the growth medium. Such a plate can be covered with a type 1 cover which permits aseptic application of a resuspended microbe and protects the medium from outside contamination during antibiotic sensitivity testing.

In other embodiments, a type 3 plate cover (FIG. 12A) equipped with a blades applicator (FIG. 12B) is used to produce the trenches and can replace the type 1 or type 2 plate covers used during growth and collection of microbe colonies. In some embodiments, once a type 3 cover is used to make trenches in the growth medium, it can be replaced with a type 1 cover.

When the re-suspended sample is centrifuged the trenches act in conjunction with centrifugation of the plate to sequentially dilute the number of microorganisms in each subsequent downsteam area of the surface of the medium between trenches. Antibiotic disks or strips are applied to the areas proximal to the apex of the triangular plate and antibiotic sensitivity is measured based on the size of the zone of inhibition of microbial growth around each antibiotic disk or strip.

The system and method disclosed herein accelerate the determination of antibiotic sensitivity of a microorganism, for example, from 1-3 days to about 4-12 hours. This is accomplished in part by use of irrigation, curettage, rinsing and centrifugal force to mobilize microbe colonies from the agar toward the apex of the plate where they are aggregated. Thus, it is unnecessary to wait for individual colonies to grow to a large size suitable for conventional collection.

Moreover, the systems disclosed herein obtain a higher concentration of microbes than conventional methods that cultivate the microorganism without harvesting and aggregating the colonies by centrifugation. Using the microbes grown and collected by centrifugation, makes it possible to distribute a suspension of the microbes over different areas of a plate forming a gradient of different microbial concentrations in different concentric areas of the same plate and to have at least one area having the proper concentration of microorganisms for application of the antibiotic strips or disks. Thus, the system described herein requires only a short incubation period to reach the appropriate microbial density to conduct an antibiotic sensitivity test and does not require a prolonged incubation period characteristic of conventional methods.

In contrast, conventional methods for determining antibiotic sensitivity of a microbe range from two to seven days, including about 1-3 days to obtain sufficient microbial colonies and another 1-3 days to determining antibiotic sensitivity.

The accelerated determination of microbial antibiotic sensitivity responds to increasing demands by hospitals and doctors and reduces the risk of empirical treatment with antibiotics prior to determination of microbial antibiotic sensitivity. The system can be operated manually or can be automated and provides a way to standardize culture conditions and determination of antibiotic sensitivity among different laboratories. The system disclosed herein provides a variety of economic benefits including reductions in the time a patient spends in a hospital and corresponding cost and labor economies in performing antibiotic sensitivity determinations.

Another advantage of the trianguloid-plate systems disclosed herein is that they are closed plate systems which reduce the risk of microbial contamination by medical technicians and personnel and which reduce the risk of contamination of a clinical sample being tested.

Various elements of the system are described below.

A trianguloid plate or dish refers to a container that can hold a non-liquid, solid or semi-solid (e.g., gel) microbial medium, such as an gel- or agar-based bacterial culture medium, and which from a top or bottom view has a piece-of-pie-shape, or which forms a sector or segment of a circle, e.g., a segment with boundaries defined by radial extensions from the center point of the circle and an arc defined by the circumference of the circle and/or a line connecting the radii at the circumference of the circle. Preferably the plate is substantially shaped like an isosceles triangle with an apex and two base points. The base comprises the two base points and may be linear or non-linear, for example, it may form a continuous convex arch between the two base points of the triangle. The angle under the apex of the trianguloid ranges from 5, 10, 20, 30, 40, 50, 60, 70, 80 or 90 degrees, but preferably ranges from about 15 to 45 degrees. The plate has substantially perpendicular walls around the periphery of its bottom surface. The plate essentially has three walls, a basal wall opposite the apical tip and two lateral, side walls which typically have identical lengths and form a triangle or trianguloid form with the basal side.

Samples include fluids obtained from patients, including fluidized solid samples. Liquid or liquefied samples can be obtained or prepared from clinical samples, such as from blood, plasma, serum, CSF, synovial fluid, saliva, mucus, respiratory fluids, bile, urine, feces, or other biological fluids or tissues. In some cases, such samples are obtained from water, including drinking water, reservoir water, riparian or sea water, food or drink, animal feeds, sewage, medical wastes, or from other environmental sources. In some embodiments, a sample is harvested, for example, with a swab, lavage, or biopsy, and then suspended in a fluid such as a growth medium prior to application to the system disclosed herein.

A microbe or microorganism includes colony-forming culturable bacteria, fungi and other eukaryotes for which it is desired to determine sensitivity to an antibiotic. These include, but are not limited to, bacteria causing serious human or animal diseases including both Gram positive and Gram negative bacteria. Examples of such bacteria are described by, and incorporated by reference to hypertext transfer protocol secure://en.wikipedia.org/wiki/List_of_clinically_important_bacteria (last accessed Mar. 25, 2020).

In some embodiments of the invention the antibiotic sensitivity of *Haemophilus influenzae, Pseudomonas aeruginosa, Streptococcus pneumoniae, Staphylococcus aureus*, or *Escherichia coli* is determined. Other antibiotic resistant bacteria may be evaluated such as methicillin-resistant *Staphylococcus aureus* (MRSA), vancomycin-resistant *Enterococcus* (VRE), multi-drug-resistant *Mycobacterium tuberculosis* (MDR-TB), and carbapenem-resistant Enterobacteriaceae (CRE) gut bacteria. These may be tested for on selective media containing one or more antibiotics to which the microbe may be resistant.

A sample or culture of a microorganism may be a fresh biological sample, a sample that has been cultured in broth or another culture medium, such as a selective growth medium for a particular microbe, or a clonal sample of a microorganism isolated away from other microorganisms. This method is generally applicable to microbes including bacteria and fungi which can be cultured on a non-liquid, solid or semisolid medium The term "medium" includes non-liquid, solid and semi-solid media, including gel-based or agar-based media such as Mueller-Hinton medium. A "non-liquid" medium may contain liquids, for example, as part of a gel, but maintains its structure under low speed centrifugation as disclosed herein. In an alternative embodiment, a highly viscous medium that may be technically considered a liquid medium may be used as long as it maintains its structure under low speed centrifugation so that microbe colonies can be collected and/or so that its surface can be trenched as disclosed herein.

Microbe culture media are often based on a gel and are usually commercially available. Examples include blood gel medium often used in petri dishes or Muller-Hinton gel medium for often used in Muller-Hinton dishes. Other commercially available microbe culture media can be used or media can be produced from their ingredients for example when a specialized medium for a particular microbe or particular culturing protocol is required.

Typically a medium will permit the growth of a microbe into colonies and permit the colonies to be separated and collected by low speed centrifugation (e.g. a speed that does not substantially separate medium from the plate or a speed which does not substantially damage the medium in the plate). A g force is selected based on a force that does not separate the medium from the plate or damage it. Advantageously a g force may be selected ranging from 30, 40, 50, 60, 70, 80, 90, 100, 120, 150 to 200 g (or any intermediate value within this range).

In one embodiment, a specifically designed centrifuge having a radius of about 300 mm, which can accommodated the trianguloid plates is employed. Approximate rpms for this centrifuge corresponding to the g force produced as shown by the table below. Those skilled in the art may select an appropriate rpm value to provide a low g force based on the radius of the centrifuge and its speed.

| RPM | G FORCE |
|---|---|
| 1000 | 200 |
| 800 | 150 |
| 500 | 75 |

In some embodiments, the medium will support the production of trenches on its surface. A suitable microbe culture medium may be selected by one skilled in the art based on the type of microorganism to be isolated or grown culture media for use as media in the system disclosed herein include Mueller-Hinton agar as well as media based on those described by, and incorporated by reference to, hypertext transfer protocol. secure://microbeonline.com/culture-media/(last accessed Apr. 6, 2020). Medium may also be produced, for example, by addition of agar, from a culture medium such as those described by and incorporated by reference to hypertext transfer medium secure://en.wikipedia.org/wiki/Growth_medium (last accessed May 19, 2020).

Culture conditions. A microbe is typically grown at its optimal pH, atmospheric composition, and temperature.

These vary and may be selected based on the microorganism to be isolated, grown and tested. A non-liquid, solid, semi-solid medium or gel-based medium may be a minimal or enriched culture medium, a selective medium, or a differential medium. Examples of media include Mueller-Hinton medium, LB medium, plate count agar, nutrient agar, trypticase soy agar, Löwenstein-Jensen medium, or a medium containing a carbon source, a nitrogen source or amino acids (e.g., yeast or beef extracts), and salts and minerals.

In the present application the terms antibiotic and antimicrobial are used interchangeably to define a chemical compound that inhibits or abolishes the growth of a microorganism and/or kills the microorganism, such as bacteria or fungi that is, a chemical compound with anti-bacterial or anti-fungal, activity. The term includes antibiotic or antimicrobial compounds produced and isolated from living organisms, for example, the penicillin-class produced by fungi in the genus *Penicillium* or streptomycin from bacteria of the genus *Streptomyces*. The term also includes antibiotic or antimicrobial compounds obtained by chemical synthesis, such as sulfonamide drugs or antimicrobial compounds made by chemical modification of a naturally occurring compound. The term in particular includes anti-bacterial antibiotics, which are antibiotics that do not have activity against viruses, fungi and other non-bacterial microbes.

The anti-bacterial antibiotics include bactericidal antibiotics, which destroy bacteria, and bacteriostatic antibiotics which prevent bacteria from multiplying. The anti-bacterial antibiotics further include "narrow-spectrum" antibiotics which target particular types of bacteria, such as Gram negative or Gram-positive bacteria, and broad spectrum antibiotics which affect a wide range of bacteria. Likewise, the anti-bacterial antibiotics include antibiotics for ingestion as well as antibiotics for intravenous administration which are often used to treat serious infections such as deep-seeded systemic infections, and antibiotics for topical administration. The anti-bacterial antibiotics comprise antibiotics within the following presently recognized classes: Aminoglycosides, Ansamycins, Beta-lactam antibiotics, (including the carbacephem, carbapenems, cephalosporins (first, second, third and fourth generations), monobactams and penicillins) Glycopeptides, Macrolides, lincosamides, Polypeptides, Quinolones, Sulphonamides, Tetracyclines, Cyclic lipopeptides, Glycylcyclines, Oxazolidinones, diaminopyrimidines, Nitrofurans, Rifamycins, antibiotic peptides, amphenicols, nitroimidazoles, streptogramins and phosphomycins. Specific classes of and individual antibiotics are described by, and incorporated by reference to, hypertext transfer protocol secure://en.wikipedia.org/wiki/List_of_antibiotics (last accessed Apr. 6, 2020). Antifungal compounds are described by, and incorporated by reference to, hypertext transfer protocol secure://en.wikipedia.org/wiki/Antifungal (last accessed Apr. 6, 2020).

Antimicrobial strips or disks (discs. wafers) are commercially available and may be selected by those skilled in the art. These include antimicrobial susceptibility test disks, strips, grids and cartridges. One type of disk is 9 mm in diameter and color coded for safe identification. Additional description of such disks or strips is available at, and incorporated by reference to hypertext transfer protocol secure://www.sciencedirect.com/topics/immunology-and-microbiology/antibiotic-disc (last accessed Apr. 6, 2020) or at hypertext transfer protocol secure://www.creative-diagnostics.com/Antimicrobial-Susceptibility-Test-Kits.htm (last accessed Apr. 6, 2020).

Minimal Inhibitory Concentration (MIC) is defined by the lowest concentration of a drug in which no visible growth occurs. The tested microorganism will be classified as clinically susceptible, intermediate or resistant to the tested drug. The interpretative standards for these classifications have been published by Clinical and Laboratory Standards Institute (CLSI) in the USA and the European Committee on Antimicrobial Susceptibility Testing (EUCAST). MIC test is the gold standard for in vitro detection of antibiotic resistance.

The methods disclosed herein may be performed manually or automated. Automation can provide a higher degree of standardization between laboratories performing the same method when machines are suitably calibrated. The methods disclosed herein may be fully or partially automated. For example, a machine can hold a trianguloid plate of the invention and dispense drops of a sample on the agar or gel-based medium in the plate; it can tilt the plate so as to distribute a sample on the medium, can hold and centrifuge a plate, and can incubate a plate. Once colonies appear the processes of rinsing and curettage and collection can also be automatically performed. Moreover, a digital camera linked to a processor can evaluate the size of zones around antibiotic test strips or disks as well as the sizes and morphologies of the microbial colonies.

Controls. A positive or negative control may be used in conjunction with the method disclosed herein. A control may constitute a strain of a microorganism having a known degree of sensitivity to one or more antimicrobial or antibiotic compounds. For example, presence of zone of inhibition in an area of the medium in the trianguloid plate as disclosed herein is not necessarily automatically interpreted as susceptibility to the antibiotic. Rather, the zone width can be measured and compared against a reference standard which contains measurement ranges and their equivalent qualitative categories of susceptible, intermediately susceptible or resistant microorganisms Plate construction. The plate and its cover are preferably produced from a thermoplastic resin, such as acrylic resin, polylactide resin, polyglycolic acid resin, styrene resin, acrylic-styrene copolymer (MS resin), polycarbonate resin, polyester resin, polyvinyl alcohol resin, ethylene-vinyl alcohol copolymer, thermoplastic elastomer, vinyl chloride resin, silicone resin, and combinations thereof. In some cases, they may comprise glass, ceramic or metal.

Plate covers. As apparent from their descriptions above, there are three types of plate covers that may be used to cover a trianguloid plate. The first type (type 1 cover) has a rubber septum and is used to apply drops of a microbial suspension. The second type (type 2 cover) has a rubber septum, drainage tip and a filter and is used to rinse and to collect the microbe colonies. The third type (type 3 cover) has a blades applicator which can cut trenches into the surface of the medium when plates with pre-cut trenches are not used or commercially available.

Embodiments of the subject matter disclosed herein include but are not limited to the following.

One embodiment of the invention is a trianguloid plate, culture plate, or dish comprising an apical tip and a broader basal end, wherein said plate comprises a bottom surface substantially having a shape of an isosceles triangle having an apex at one end and a base comprising the other two points of the triangle at the other end, and walls around, and substantially perpendicular to, the bottom surface defining an enclosed trianguloid compartment suitable for containing a microbe medium. Preferably, the trianguloid plate, its cover, clips and other elements are integrated into a trianguloid culturing and centrifuging system, such as that depicted by the figures, e.g., a centrifugation accumulated colonies triangular agar technology (CAC-TAT) plate or system.

The plate may be formed from a thermoplastic resin in an integrated manner and equipped with a cover that is also so formed. The thermoplastic resin may be at least one material selected from the group consisting of acrylic resin, polylactide resin, polyglycolic acid resin, styrene resin, acrylic-styrene copolymer (MS resin), polycarbonate resin, polyester resin, polyvinyl alcohol resin, ethylene-vinyl alcohol copolymer, thermoplastic elastomer, vinyl chloride resin, silicone resin, and combinations thereof.

In some embodiments, the base of the trianguloid plate, which is opposite the apical tip, comprises a convex arc between the two points and the plate substantially has the shape of a segment, sector, or pie-slice of a circle.

In some embodiments, the angle α at the apical tip of the plate or cover ranges from 15, 20, 25, 30, 35 or 45 degrees or any intermediate angle.

In some embodiments, the plate has a length measured from its apical tip to a midpoint of the basal side of the plate ranging from 5, 10, 15, 20 or 25 cm, preferably about 10 to 20 cm, and a width at its base ranging from 5, 10, 15, 20, 25, 30, 35, to 40 cm, preferably about 5 to 30 cm, wherein the walls have a height ranging from 0.25, 0.5, 1.0, 1.25, 1.5, 1.75, to 2.0, 3.0, 4.0, to 5.0 cm, preferably about 1 to 3 cm. or any intermediate value within these ranges.

In some embodiments, the bottom surface further comprises anchors or ridges which extend from the bottom surface into the trianguloid compartment and which are substantially perpendicular to the bottom surface. Preferably, these anchors or ridges are integrally formed with the plates. These anchors or ridges may extend from about 10, 20, 30, 40, 50, 60, 70, 80, 90 or >90% of the height of the plate, preferably about 30 to 50% of the height of the plate walls. Preferably, these anchors or ridges do not penetrate the surface of the medium or the bottoms of trenches in the medium. The number and distribution of these anchors or ridges may be selected based on the type and viscosity or gel strength of a medium and on the speed of centrifugation so as to stabilize the medium in the plate during centrifugation. In some embodiments the stabilizing ridges or anchors will be spaced about 1, 2, 3, 4, 5, 6, 7, 8, 9, or 10% the length and/or width of the plate. Preferably, the level of medium fill in the plate covers these ridges or anchors. In a preferred embodiment, the fill of the medium does not exceed 70-80% of the wall height of the plate and, when anchors or ridges are present, the fill covers them to another 20, 25, 30, or 35% of wall height.

Another aspect of the invention is a trianguloid plate as disclosed herein in combination with a cover that fits over the walls of the plate and, optionally, one or more clips or other attachments configured for securing the cover to the walls. Thus, a trianguloid plate can further comprise a cover that fits on, in and/or over the walls of the plate, which cover further comprises a septum area, e.g., made of rubber or other preferably resealable polymer such as a silicone rubber or non-porous membrane material through which a liquid sample may be injected into the compartment. The septum area is preferably configured to permit injections by puncture without permitting the ingress or egress of material into the trianguloid plate other than the material being injected. The cover may be made out of a same or different material than the plate and preferably is transparent to permit observation of microbial growth on medium in the plate without having to remove the cover and risk contamination.

The septum portion of the cover is typically positioned over a central portion of the distal, basal portion of the cover opposite the apical tip near the basal portion of the cover so as to permit deposit of a sample on to a medium near the basal portion of the plate. In a plate having areas defined by concentric troughs, it may be positioned over Area 1 of a plate to the basal end of the plate. The septum may be of any shape that permits injection of a sample through it into the plate or on to medium in the plate, while maintaining the integrity of the cover and plate so as to exclude contaminants. In some embodiments it will be a rectanguloid slot concentric with the basal end of the cover or plate, for example, having a length of about 0.25 to 0.5 cm as measured along the length of the cover from apical tip to basal end and a width of about 0.5, 1, 2, 3, 4, to 5 cm as measured between the lateral sides of the cover. In other embodiments, the septum may be round, ovoid, square, rectangular, or triangular. In some embodiments, the area of the septum is not more than 0.5, 1, 2, 3, 4, or 5% of the total area of the cover.

Preferably, from the viewpoint of stabilizing and retaining a medium within the plate during centrifugation, the bottom surface of the plate further comprises substantially perpendicular anchors or ridges which extend from the bottom surface into the interior compartment formed by the bottom surface of the plate and the walls of the plate.

In some embodiments, the apical tip of the plate further comprises an opening through which liquid can pass, which is, optionally, operatively connected to a filter that retains colonies of the microorganisms. Preferably, the opening and filter will pass spent washing liquid, such as water or a saline rinse solution, but retain microbial colonies or microbes, thereby accumulating and concentrating microbial colonies at the apical tip of the system after centrifugation or rinsing.

Typically, during use the trianguloid compartment of the plate further comprises a non-liquid medium which covers the bottom surface of the plate. In some embodiments, the medium will fill to at least 10, 20, 30, 40, 50, 60, 70, 80, or 90% of the height of the plate. When anchors or ridges attached to or integrally formed with the bottom of the plate are present, which help stabilize the non-liquid medium during centrifugation, the fill volume or height of gel or other solid or non-liquid medium preferably exceeds their height by at least 10, 20, or 30% of the height of the plate.

The non-liquid medium in the compartment formed by the bottom surface and walls of the plate may be scored with one or more trenches which typically are arced from one side of the plate to the other. The most distal (from the apical tip) trench may be wider than other trenches closes to the apical tip. In some embodiments, the medium in the compartment of the plate comprises 4 to 6 concentric trenches between equilateral positions on the side walls of the plate which trenches demark 5 to 7 separate concentric areas on the surface of the medium. In one embodiment the first trench which is most distal from the apical tip is about 3-5 mm wide, preferably about 4 mm, and about 0.8 to 1.2 mm, preferably about 1 mm, deep and the other 3 to 5 trenches are about 0.8 to 1.2 mm, preferably about 1 mm, wide and deep.

The trenches scored in the non-liquid medium in the plate can be spaced at approximately equal intervals along the distance between the apical tip and the midpoint of the base of the trianguloid plate. Typically, the trenches are spaced at approximately equal distances from one another, though the spacing can be varied to attain a particular distribution of a microbial sample over the various areas in the plate.

Figure 12A:
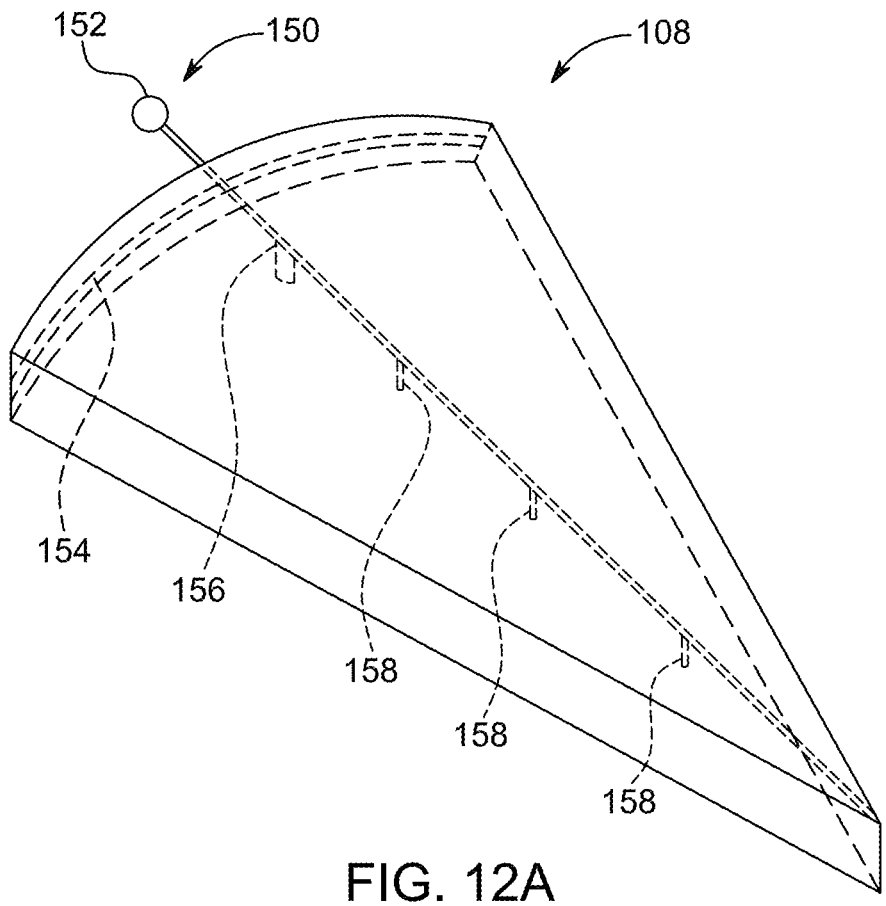
FIG. 12A depicts an embodiment of the system that includes a cover (cover 3) having a blades applicator holder 152 and blades applicator 150 which comprises large blade 156 and narrow blades 158 for forming trenches in a non-liquid medium contained within the plate. In this embodiment, cover 108 contains opening 154 through which the blades applicator 152 fits.
Figure 12B:
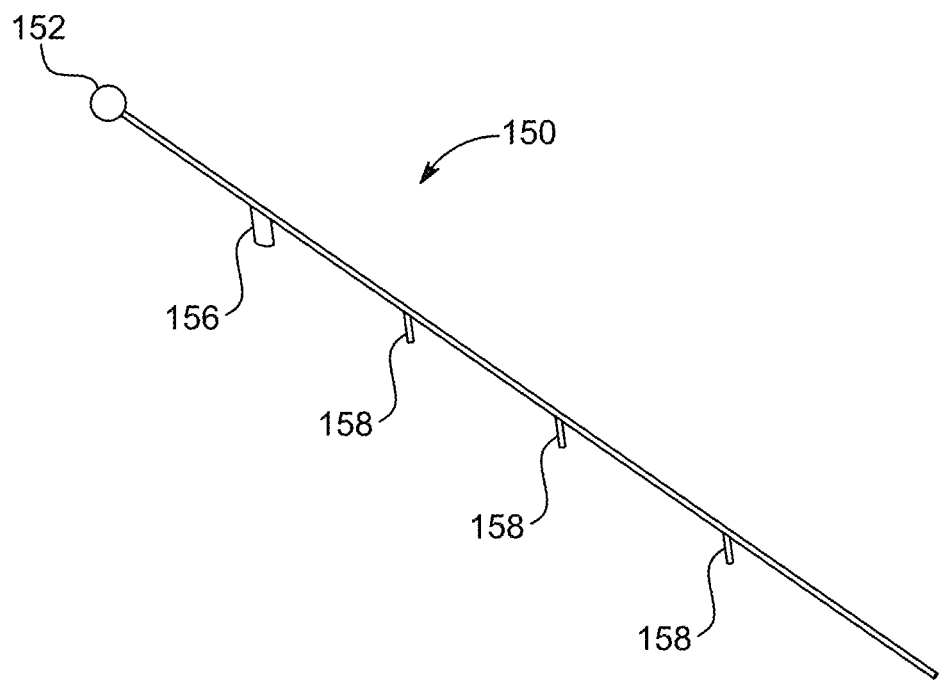
FIG. 12B depicts the blades applicator 150 with holder 152 and blades 156 and 158.

In some embodiments, the cover of the plate, or the basal edge of the plate, may be modified to contain a blades applicator which can be manipulated to form the trenches on the surface of a non-liquid medium in the plate as shown by FIGS. 12A and 12B.

Figure 15:
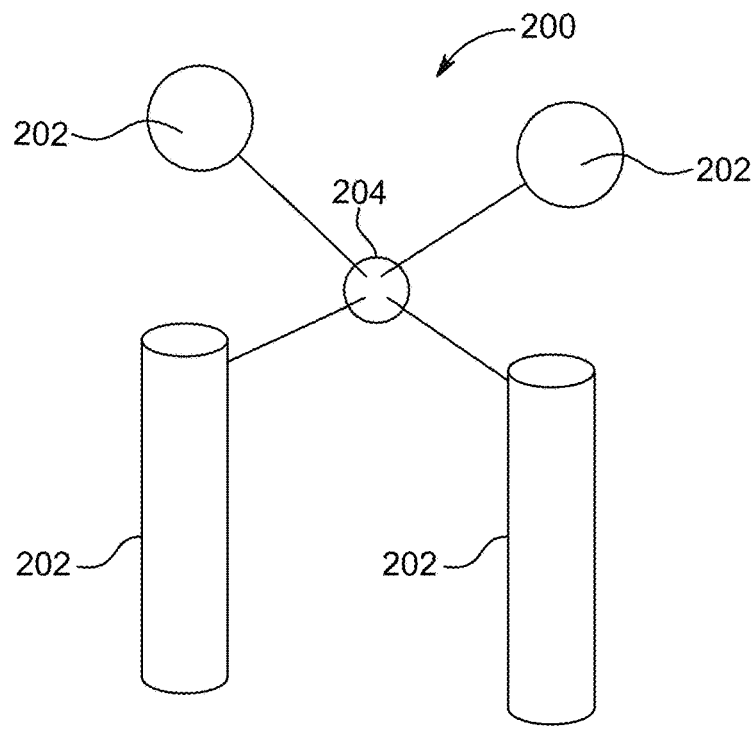
FIG. 15 depicts a centrifuge tube case 202 and the axis of rotation 204 for the centrifuge 200.
Figure 16:
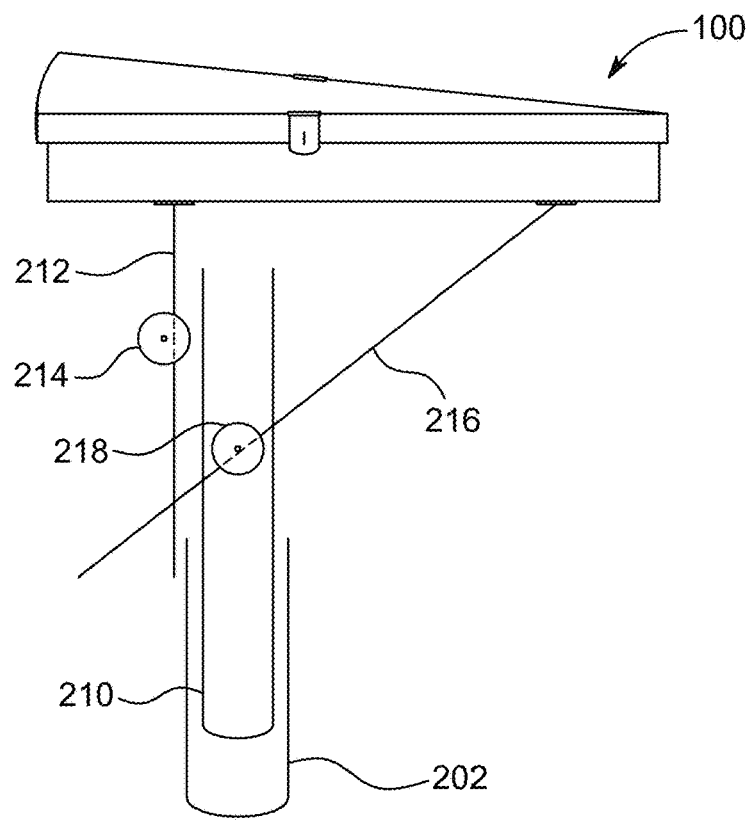
FIG. 16 depicts an adaptor to hold trianguloid culturing and centrifuging system 100 during centrifugation. As shown, expanding bar to adjust the plate vertically 212, knob to adjust the plate vertically 214, expanding bar to adjust the horizontal angle 216 and knob to adjust the horizontal angle 218.

Another embodiment of the invention is directed to a kit comprising the plate and cover, and/or at least one of a sample containing a microorganism in suspension, a syringe suitable for applying the sample of the microorganism to the medium in the plate, a centrifuge configured to rotate the plate with its apical point oriented outward from the axis of the centrifuge and the area of rubber or other material through which a liquid sample may be injected proximal to the axis of rotation of the centrifuge, or an adaptor to securely fit the trianguloid culturing and centrifuging system into a centrifuge and orient the apical tips of the plates outward from an axis of rotation of the centrifuge. The kit may further comprise an adaptor such as that shown by FIGS. 15 and 16 to facilitate loading, positioning, and centrifugation of the culture plates. In one embodiment, the adaptor securely fits the trianguloid culturing and centrifuging system disclosed herein into a centrifuge so as to keep the system substantially flat with respect to the ground and so as to orient the apical tip of the system outward at a 90 degree angle from the axis of rotation of the centrifuge rotor, wherein said adaptor comprises a plate or other holder that securely clips or otherwise attaches to the exterior bottom of the system, said plate being attached to a hinge which attaches to the centrifuge rotor and which is adjustable so as to keep the system flat during centrifugation, said hinge being optionally attached to the centrifuge rotor via blank centrifuge tube which fits into a tube holder or tube case of a centrifuge.

Another embodiment of the invention involves a method for preparing a sample containing a microorganism for antibiotic sensitivity testing comprising applying an amount of said sample sufficient to cover a culture area between the basal end of the plate and the at least one trench; culturing the sample under conditions suitable for formation of microbial colonies; loosening the resulting microbial colonies and consolidating the colonies by centrifuging the plate with the apical end of the plate oriented next to the axis of the centrifuge; collecting the colonies from the apical end of the plate; and resuspending the collected colonies in medium that maintains their viability.

In some embodiments of this method, microbial colonies are loosened by irrigation in a saline solution followed by curettage of the colonies to remove them from the medium. In another embodiment, the colonies growing on the plate are loosened by irrigation with a saline solution followed by rinsing with a saline solution to detach the colonies from the medium.

Another embodiment of this method comprises applying at least one drop of a broth culture containing the microbe to an area of the non-liquid medium at the basal side of the trianguloid plate, or when trenches are present, to Area 1 of the medium between the basal side of the plate and the first trench, securing the cover to the plate with the clips on each lateral side of the cover, centrifuging the plate with its apex oriented away from the axis of centrifugation for a time and at a force sufficient to distribute the at least one drop of the broth culture on the surface of the medium, incubating the distributed sample for 4-12 hours at 37° C., and observing microbial colonies on the surface of the non-liquid culture medium. This method may further comprise injecting a saline solution through the septum in the cover to loosen the microbial colonies and curettaging the microbial colonies to remove them from the surface of the medium while removing excess fluid via a drainage tip at the apical tip of the plate or cover, and centrifuging the covered plate with its apex oriented away from the axis of centrifugation for a time and at a force sufficient to collect the loosened and curettaged colonies at the apical tip of the plate. It may also further comprise producing a suspension of the colonies collected at the apical tip by centrifugation. This can be performed by applying a continuous rinsing and removing excess fluid via a drainage tip at the apical tip of the plate or cover (cover 2) and harvesting the colonies from the triangle tip as the filter is keeping it from removing with excess fluid via drainage tip at the apical tip of the plate.

This method may further comprise testing the resuspended microbial colonies for antibiotic sensitivity by applying the resuspended microorganism to a culture area between the basal end of the plate and the first trench most distal from the apical end (e.g. Area 1), wherein said plate comprises at least four trenches which demarks at least five concentric areas on the surface of the culture medium and centrifuging the plate to distribute the microorganism over each area; applying an antibiotic disk, strip or other depot to at least one area other than the first area where the sample was applied; culturing the microorganism for a time and under conditions sufficient to detect bacterial growth; and selecting an antibiotic sensitive microorganism when there is a clear or no-growth area around the antibiotic disk, strip, wafer, or other depot.

Another embodiment of this method for determining sensitivity of a microbe to an antibiotic comprises applying at least one drop of a broth culture containing the microbe to an Area 1 of non-liquid culture medium in a covered trianguloid plate, where the surface of the medium comprises at least five concentric trenches defining Areas 1, 2, 3, 4, 5 and 6, wherein the cover may be secured to the plate via a clamp on each lateral side of the cover, and wherein the at least one drop is aseptically injected through a septum in the cover of the plate onto the Area 1, centrifuging the plate with its apex oriented away from the axis of centrifugation for a time and at a force sufficient to distribute the at least one drop of the broth culture on the surfaces of Areas 1, 2, 3, 4, 5 and 6 of the non-liquid medium, applying at least one antibiotic disk or strip to at least one of Areas 2, 3, 4, 5 or 6 of the medium, incubating the covered plate containing distributed sample for 4-12 hours at 37° C., measuring a zone of inhibition around the one or more antibiotic disks or strips, and selecting a microbe that is sensitive to the antibiotic on the disk or strip when a zone of inhibition is observed.

In another embodiment of this method a microbe suspension having a McFarland density strength (turbidity) of 0.5 is produced from a large microbial colony or from centrifugally aggregated and harvested microbes by using a triangular-plate as disclosed herein. For example, the microbial colonies may be grown, detached, and curettaged using a saline soak and/or rinse (e.g., 0.25, 0.5 up to 1.0 normal saline) and resuspended in a suitable solution that maintains microbial viability, such as in half normal saline. This suspension is distributed over different areas of the medium in a triangular plate which forms a lawn or microbial background of suitable density for assessing antibiotic sensitivity to antibiotic strips or disks placed on it.

In this embodiment, an amount of the microbe suspension corresponding to 1, 2, 3, 4, 5 to 6 of the suspension equivalent in volume to drops dispensed by a 21 gauge needle is deposited on an Area 1 of the medium in a covered CAC-TAT plate with trenches, where the surface of the medium comprises at least five concentric trenches defining Areas 1, 2, 3, 4, 5 and 6, wherein the cover may be secured to the plate via a clamp on each lateral side of the cover, and wherein the at least one drop is aseptically injected through a septum in the cover of the plate. One skilled in the art may select an appropriate amount of microbe suspension to provide a gradient of microbes on different areas of the plate, for example, a volume equivalent to a particular number of drops from a 21 gauge needle, to apply to Area 1 based on factors including the size of the plate and Area 1, the depth and width of trenches, the g force applied by centrifugation, the type or dryness of the medium in the plate and the type of microbe being cultured on the medium.

Next the plate containing the drops of microbe suspension in Area 1 is tip side-to-side to spread the drop(s) over Area 1.

Subsequently, the plate with the drops distributed over Area 1 is centrifuged at 400-800 rpm for 5-10 minutes to provide a graduated spread the microbial suspension in Area 1 over all the trenches into Areas 2, 3, 4, 5 and 6 of the plate. The plate is centrifuged with its apex oriented away from the axis of centrifugation for a time and at a force sufficient to distribute the drops of the colony suspension on the surfaces of Areas 1, 2, 3, 4, 5 and 6 of the gel or solid medium.

After the graduated distribution of the microbe suspension over the areas of the medium defined by the concentric trenches, an antibiotic strip or disk is applied to areas on the medium, such as the last 2 or 3 areas, and the plates are incubated for 4 to 12 hours.

After this period of incubation the zones of inhibition formed around the antibiotic strips or disks are observed. Advantageously, this method permits the formation of zones of inhibition within a few hours and not days.

EXAMPLES

Validation Data and Challenges for CAC-TAT

Example 1: Effect of Centrifugation on Spreading of the Cells Suspension

Figure 5:
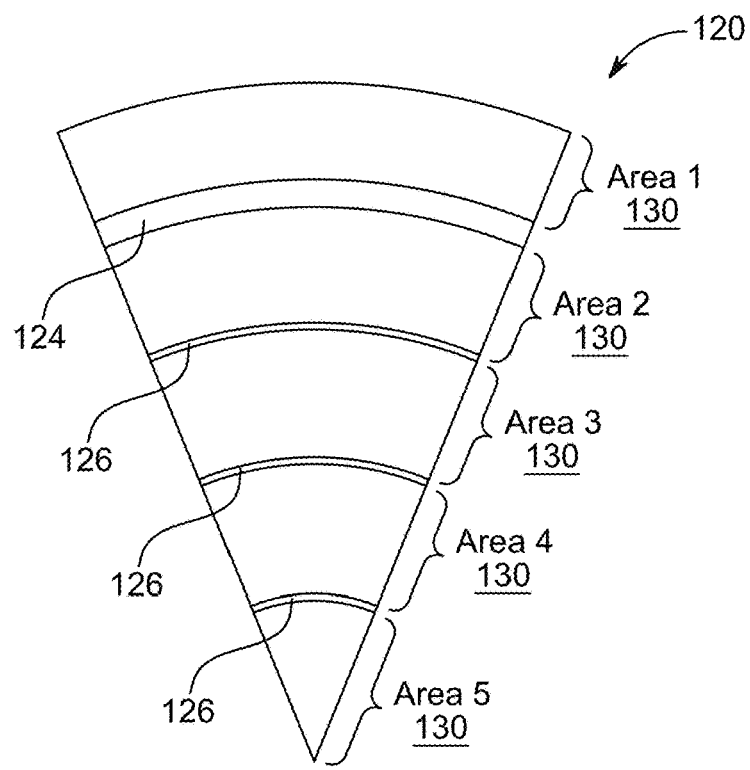
FIG. 5 provides a top view of a plate 120 containing non-liquid medium with a wide distal trench 124 and three narrower proximal trenches (to the apical tip) 126 defining concentric surface areas 130.
Figure 6:
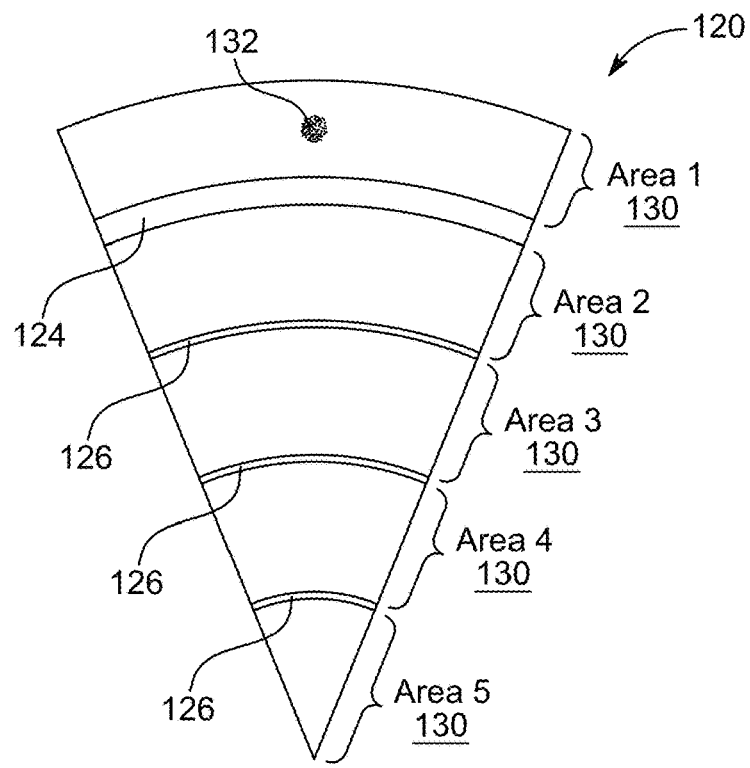
FIG. 6 depicts the plate of FIG. 5 with a sample 132 applied to the most distal concentric area 130. When a 21 gauge needle is used to apply the sample, 1-9 drops, preferably 6 drops, is applied.
Figure 7:
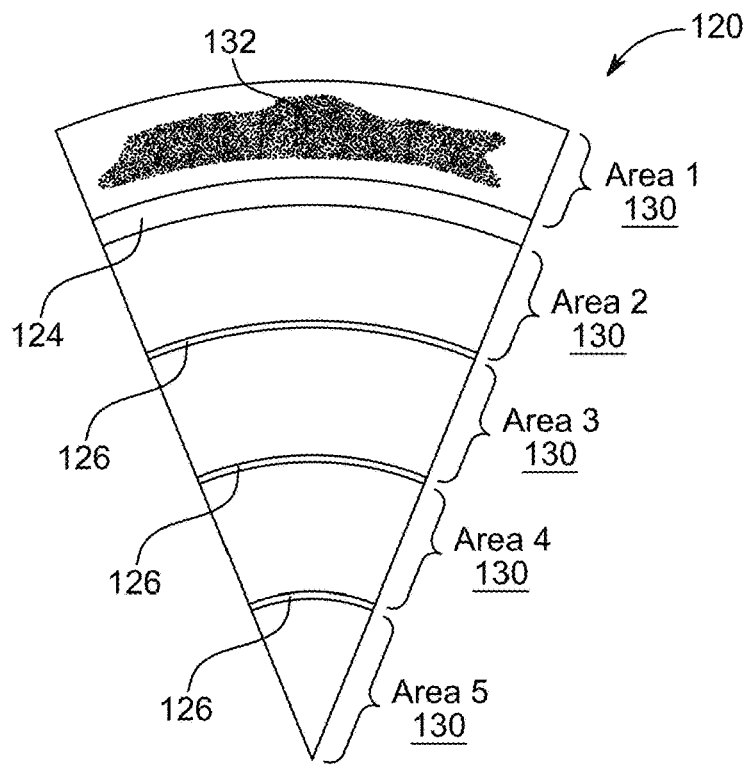
FIG. 7 shows a spread of the sample 132 on the most distal concentric area 130. In some embodiments, spreading is accomplished by tilting the plate to both sides.
Figure 8:
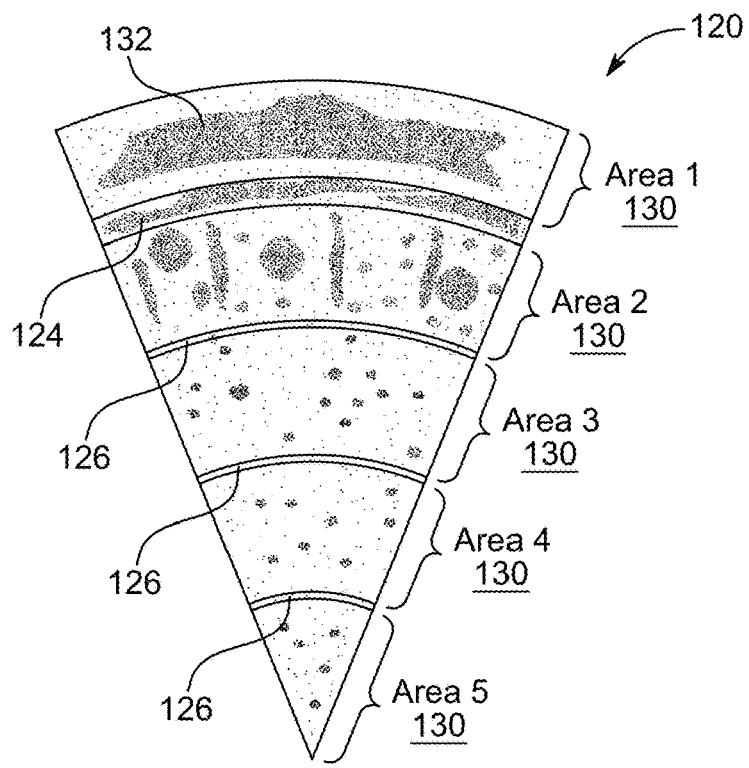
FIG. 8 shows microbial colonies growing on more proximal (to apical tip) concentric areas 130 after centrifugation of the plate as shown by FIG. 7. In some embodiments, the microbial colonies are incubated at 37° C. for 4-12 hours.
Figure 9:
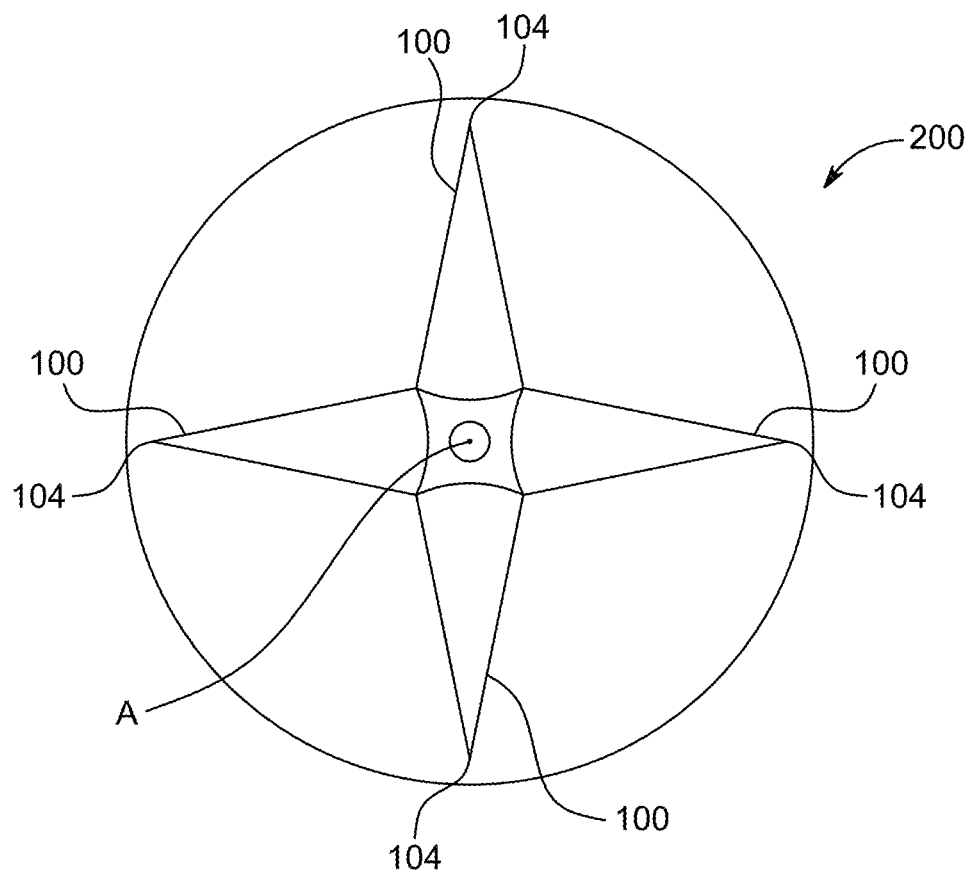
FIGS. 9 and 10 depict the orientations of four trianguloid culture and centrifuge systems 100 in a centrifuge 200 where the apical tips 104 are pointed outward from the rotational axis of the centrifuge.
Figure 10:
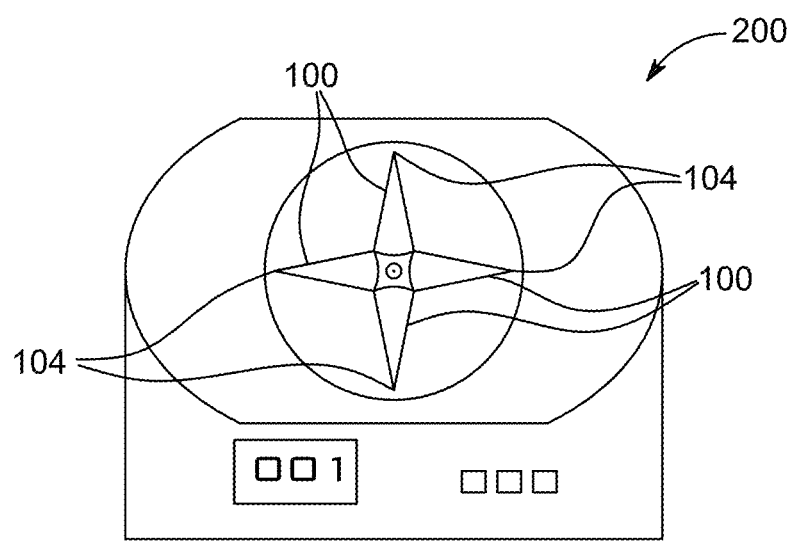
Figure 11:
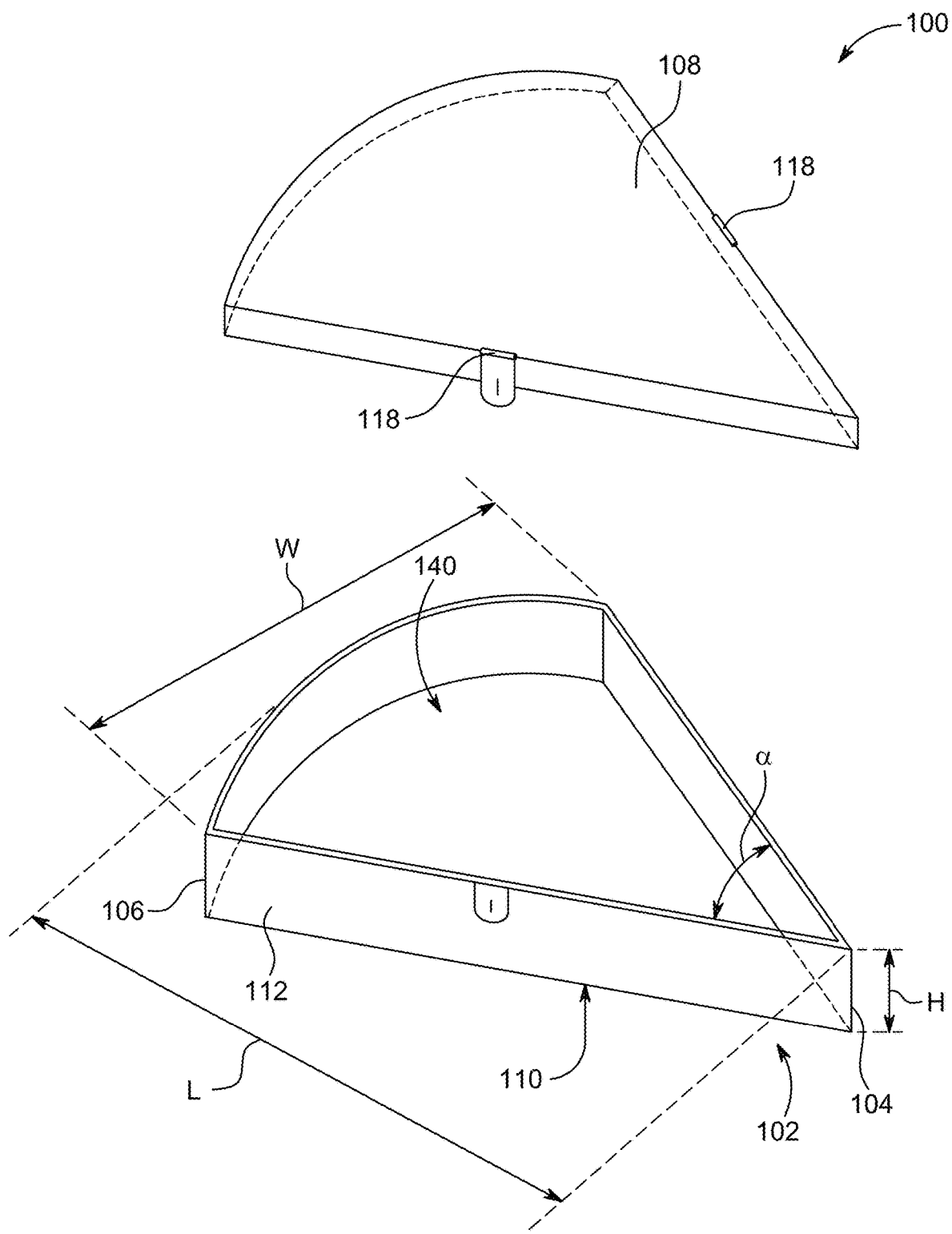
FIG. 11 depicts an exploded diagram of the cover 108 and hinges 118 and the lower plate 112 portion which indicates the length, width and height dimensions as well as the angle, α, of the apical tip. The walls 112 and bottom of the plate 110 form a compartment 140 which can accommodate a non-liquid medium.

To test the effects of centrifugation on spreading of a cell suspension, six drops of a microbial suspension at a McFarland concentration density of 0.5 injected from a 21 gauge needle through the septum onto non-liquid medium in Area 1 of a trenched as described in FIGS. 5-7. The plates were then centrifuged at 200, 500, 800 or 1,000 rpm for 10 minutes. The amount of the microbial suspension spread to the triangular apex of each plate was measured and the percentage of medium in the plate destroyed by centrifugation were determined and shown in the table below.

| Centrifugation speed | % of spread to triangular apex | Problem % of gel destruction |
| --- | --- | --- |
| 200 RPM | 30% | 11% |
| 500 RPM | 88% | 34% |
| 800 RPM | 91% | 81% |
| 1000 RPM | 95% | 100% |

Example 2: Gel Stability Test after Adding Obstacles

Figure 3:
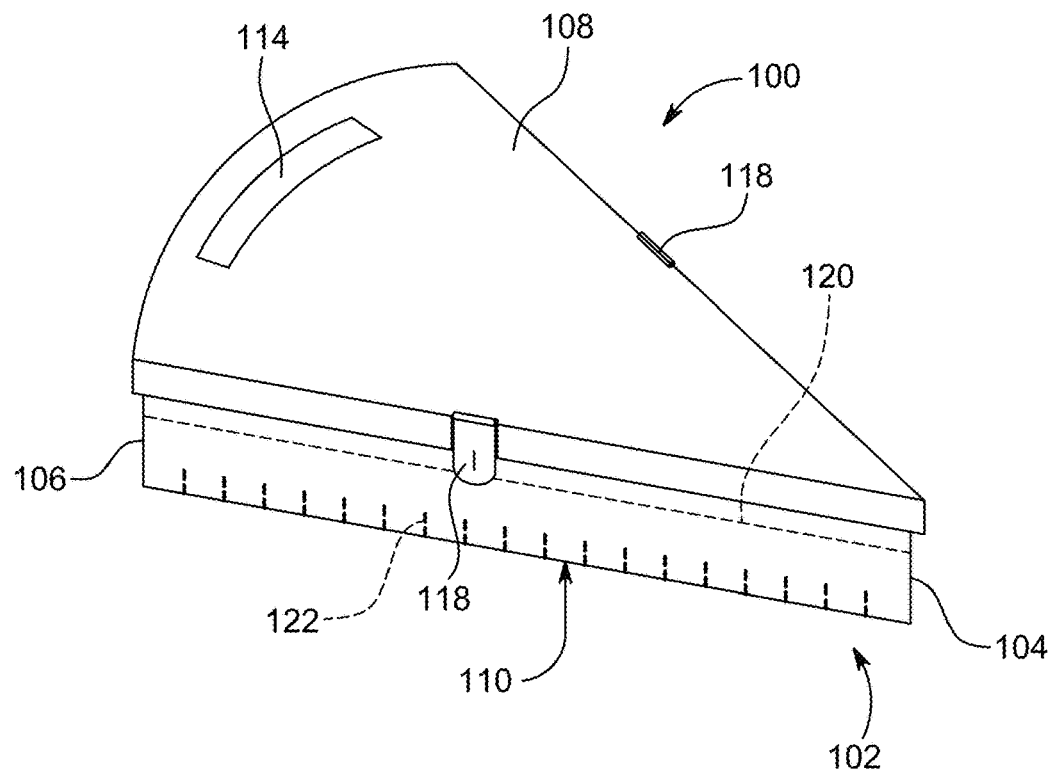
FIG. 3 shows side view of the trianguloid culturing and centrifuging system 100 having apical tip 104 and basal end 106. In this embodiment, the bottom surface of the plate 110 comprises anchors or ridges 122 which extend upward and which secure nonliquid medium 120 in the plate 110.
Figure 4:
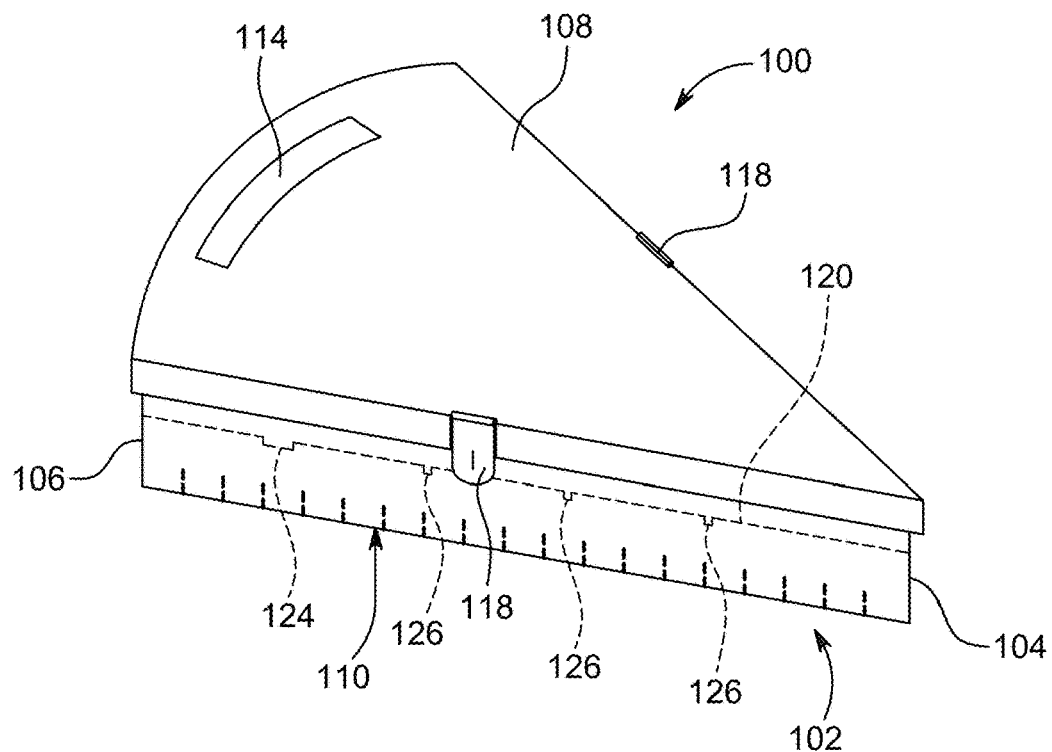
FIG. 4 shows a side view of the trianguloid culturing and centrifuging system 100 similar to that described by FIG. 3 except that the non-liquid medium comprises a most distal (from apical tip) trench 124 and narrower more proximal trenches 126 in the solid medium 120.

As shown by FIGS. 3 and 4, wall-shaped obstacles about 3 mm in height were attached to the bottom of the plates over which gel was embedded. Covers were placed on the plates. The stability of the gel in the plates to centrifugation was determined after the plates were centrifuged at different speeds with their pointed ends extended outward as shown in the table. As shown, the obstacles made it possible to stabilize 100% of the gel in the plates at speeds less than 800 rpm. However, over 90% of unsecured covers floated on top of the plates

| Centrifuging speed | % of plates stabilized its gel | Other problems |
| --- | --- | --- |
| 200 RPM(round per minutes) | 100% | Cover float in 90% |
| 500 RPM | 100% | Cover float in 100% |
| 800 RPM | 92% | Cover float in 100% |
| 1500 RPM | 61% | Cover float in 100% |

Example 3: Plate Cover Stabilization

Figure 1:
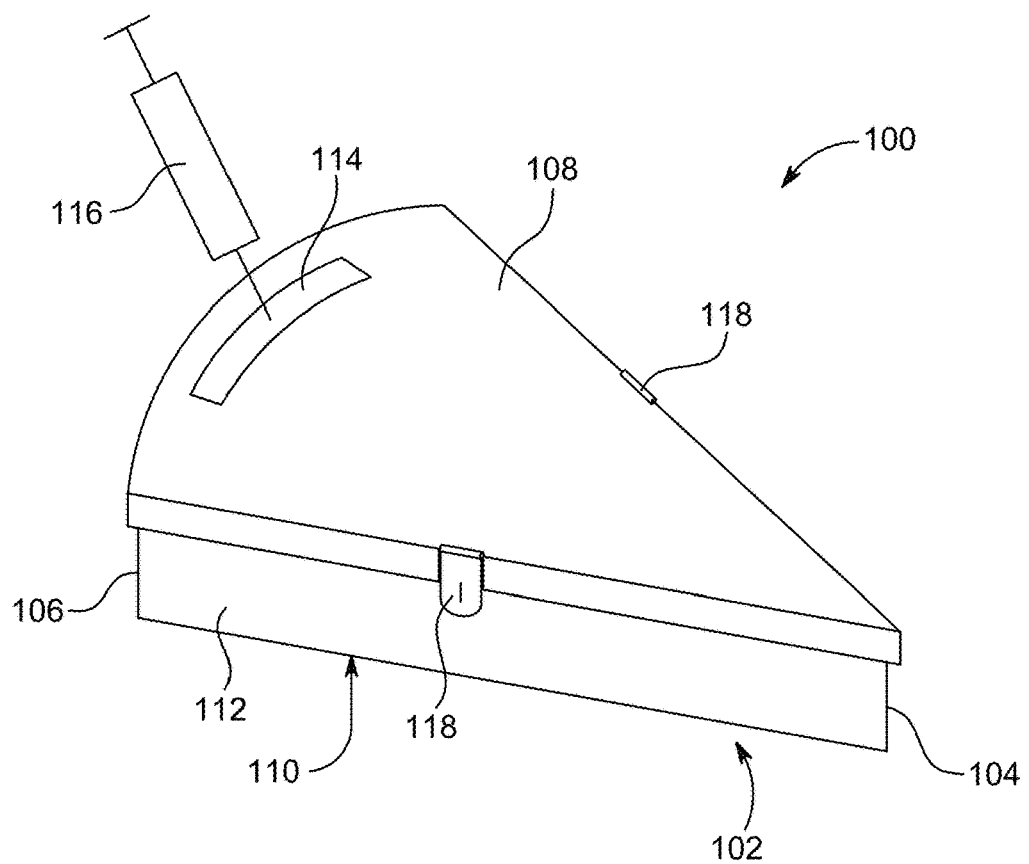
FIG. 1 depicts an embodiment of trianguloid culturing and centrifuging system 100. The system comprises a plate 102 having a bottom surface 110 and walls 112; a cover 108 having an injectable septum 114 near its basal end 106 through which a sample may be aseptically injected into the plate using a syringe 116. The trianguloid plate and its cover have an apical tip 104 and a broader basal end 106.
Figure 2:
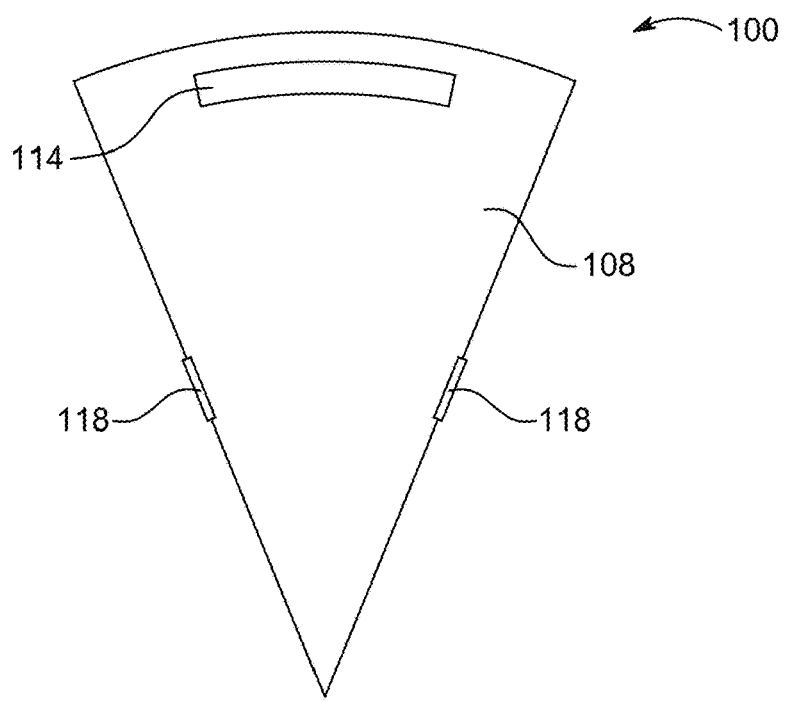
FIG. 2 shows a top view of the trianguloid culturing and centrifuging system 100 including cover 108 (type 1 cover) having an injectable septum 114 and clips 118 which secure the cover to the plate.

The effect on cover float of securing the plate covers on each lateral side of the plates was determined under conditions identical to those in EXAMPLE 2 above. As also shown by FIGS. 1 and 2, covers of plates that were clipped at each side of the plate were stable during centrifugation even in high speeds:

| Centrifuging speed | % of cover stabilized (not floating) |
| --- | --- |
| 200 RPM | 100% |
| 500 RPM | 100% |
| 800 RPM | 100% |
| 1500 RPM | 100% |

Example 4: Evaluation of Plate Shape on Spread of Cell Suspension

A variety of different shaped plates as described in the table below were tested to determine the extent of spreading of 6 drops of a microbe suspension from gauge 21 needle of a cell suspension after centrifugation at 800 rpm for 10 minutes.

| Plate shape | Spread of suspension after centrifuging |
| --- | --- |
| circular (petri dish) | Peripheral spread, no points of collections. |
| rectangular | Peripheral spread, no points of collections |
| square | Peripheral spread, no points of collections |
| pentagon | Uneven spread, more collection at angles tips. |
| trapeze | Uneven spread, more collection at angles tips. |
| hexagon | Uneven spread, more collection at angles tips. |
| semicircle | Peripheral spread, no points of collections |
| crescent | Peripheral spread, more collections at angles tips. |
| cross | Peripheral spread, no points of collections |
| heart | Uneven spread, more collection at angles tips. |
| rhombus | Uneven spread, more collection at angles tips. |
| scalene | Peripheral spread, more collection at angles tips. |
| Right angle | Peripheral spread, more collection at angles tips. |
| star | Peripheral spread, more collection at angles tips. |
| triangle | Peripheral spread, more collection at angles tips. |

These results showed that a cellular suspension collects at tips of angular plates.

Example 5: Effect of Centrifuging Triangular Plate with Base Near Axis of Centrifuge Six drops of a cellular suspension were placed in a slot in gel near the base of a trianguloid plate. The base of the plate was attached near the axis of the centrifuge with the apex of the triangular plate facing outward. The plates were spun at 800 rpm for 10 minutes and the spread of the cellular suspension on the gel was determined, see FIGS. 7-10. As shown, this procedure spread the cellular suspension toward the apex of each triangular plate.

Example 6: Effect of Gel Trenches

Six drops of a cellular suspension were placed in a slot in gel near the base of the triangular plate with a 21 gauge needle. The gel had concentric trenches (1 mm wide×1 mm deep) as shown in FIGS. 5-8. The base of the plate was attached near the axis of the centrifuge with the apex of the triangular plate facing outward. The plates were spun at 200, 500 and 800 rpm for 10 minutes and the effects of the gel trenches on spread of the cellular suspension on the gel were determined and are shown below.

| Centrifuging speed | Effects of trenches | Problems |
| --- | --- | --- |
| 200 RPM | The suspension hardly passes the second trench. | The density of the suspension is thick in both areas. |
| 500 RPM | The suspension pass all trenches | The density of the suspension is less in last area. |
| 800 RPM | The suspension pass all trenches | The density of the suspension is less in last area. |

It was found that centrifuging speeds of 500 and 800 RPM for 10 minutes were appropriate to perform spread of suspension to all areas and that gel trenches progressive reduced the density of the suspension for areas behind each additional trench.

Example 7: Effect of 4 Trenches Vs 6 Trenches Using a 4 mm Width Initial Trench

Spreading of 6 drops of cellular suspension using a needle of gauge 21 as described above was performed except that the initial trench (closest to the axis of the centrifuge) was widened to 4 mm and had a depth of 1 mm. As shown in the table below and by FIGS. 7, 8 and 13, the wider peripheral trench reduced suspension density in zones when 4, and 6 gel trenches were used.

| | 4 trenches triangle | 6 trenches triangle |
| --- | --- | --- |
| 1st area: prior to $1^{st}$ trench. | Dense suspension. | Dense suspension. |
| $2^{nd}$ area: after the $1^{st}$ trench. | Reduction in density by about 30% by vision. | Reduction in density by about 30% by vision. |
| $3^{rd}$ area: after $2^{nd}$ trench. | Further reduction in density by about 10% by vision | Further reduction in density by about 10% by vision |
| $4^{th}$ area: after $3^{rd}$ trench. | Further reduction in density by about 10% by vision. | Further reduction in density by about 10% by vision |
| $5^{th}$ area: after $4^{th}$ trench. | Further reduction in density by about 10% by vision. | Further reduction in density by about 10% by vision |
| $6^{th}$ area: after $5^{th}$ trench. | | Further reduction in density by about 10% by vision |
| $7^{th}$ area: after $6^{th}$ trench. | | Further reduction in density by about 10% by vision |

These data show that areas having lower density of cells suspension can be obtained using the trench orientations described above. Diminishing concentrations of cells were observed in both plates having six trenches and of four trenches. These results show that plates having multiple trenches can provide a gradient distribution of microbes over different surface areas of a plate using centrifugation.

Example 8: Evaluation of Plates with Applied Antibiotic Strips

Figure 13:
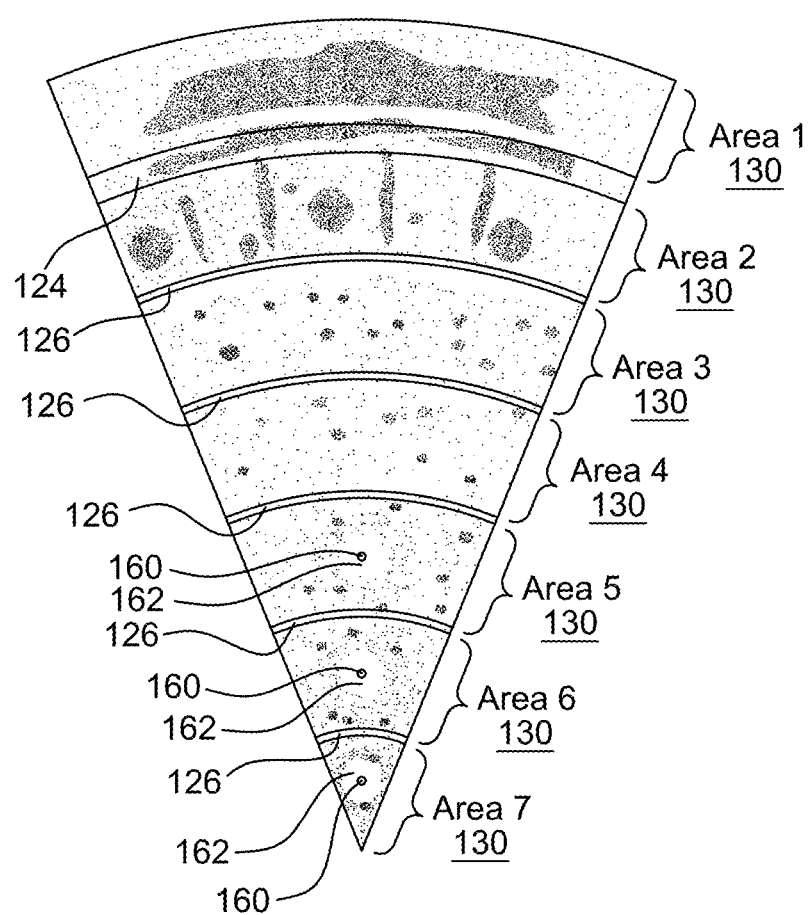
FIG. 13 depicts a plate having wide distal trench 124 and 5 more proximal narrow trenches 126 which define seven concentric surface areas 130 on the non-liquid medium. Antibiotic disks or strips 160 have been applied to the three lower (closest to apical tip) areas and are surrounded by areas 162 with no or inhibited microbial growth.

Six drops of suspension of bacteria colonies at a McFarland density of 0.5 were applied to trianguloid or wedge-shaped plates. The plates were centrifuged as described above and antibiotic strips (disks) were applied to zones near the apex of the wedge-shaped plates as shown by FIG. 13. The plates were incubated at 37 degrees centigrade for 4-12 hours and efficacy of the antibiotic strips evaluated in different areas of the trianguloid plates having different concentrations of bacteria. Results are shown below.

| Triangle areas | 4 trenches triangle | $6^{th}$ trenches triangle |
| --- | --- | --- |
| $1^{st}$ area: prior to $1^{st}$ trench. | Not working | Not working |
| $2^{nd}$ area: after the $1^{st}$ trench. | Not working | Not working |
| $3^{rd}$ area | Not working | Not working |
| $4^{th}$ area | Not working | Not working |
| $5^{th}$ area | The sensitive antibiotic is working and showing a hollow of clearness around the strip. | A zone of inhibition is detected around the antibiotic strips showing efficacy of placing the strip in the $5^{th}$ area. |
| $6^{th}$ area | | A zone of inhibition is detected around the antibiotic strips showing efficacy of placing the strip in the $6^{th}$ area |
| $7^{th}$ area | | A zone of inhibition is detected around the antibiotic strips showing efficacy of placing the strip in the $7^{th}$ area |

These data show that antibiotic strips inhibit bacterial growth when applied in an area having a moderate concentration of the microbial suspension in contrast to areas having higher concentrations of bacteria.

Example 9: Mobilizing Visible Bacterial Colonies to Plate Tip (Apex)

Six drops from broth culture suspension of bacteria were applied to wedge-shaped plates using a 21 gauge needle as described above. The plates were then centrifuged to distribute the bacteria and after centrifugation were incubated as described above at 37 degrees centigrade for 4-12 hours. Numbers of bacterial colonies moved to the tip (apex) of the plate were determined.

| Speed of centrifuging | % of colonies mobilized |
|---|---|
| 200 RPM | 0% |
| 500 RPM | 0% |
| 800 RPM | 4% |

These data show the adhesiveness of bacterial colonies to the gel and that centrifugation of the plate is insufficient to mobilize these colonies.

Example 10: Reduction of Bacterial Colony Adhesiveness and Harvesting (Irrigation and Curettage Method)

A microbial suspension was applied to trianguloid wedge-shaped plates and colonies grown on the plates as described for EXAMPLE 9. Once grown, plates were irrigated for 30 mins with distilled water, half normal saline, or normal saline solution (0.9% NaCl). The colonies were then mobilized by curettage, Results appear in the table below:

| Fluid type | % of colonies mobilized by curettage |
|---|---|
| Distilled water | 50% |
| Half normal saline | 90% |
| Normal saline | 90% |

These data show that the adhesiveness of microbial colonies can be reduced by irrigation with sterile saline fluids and that colonies can be easily detached by curettage after irrigation with saline solutions.

Example 11: Effects of Post Irrigation Rinsing (Irrigation and Rinsing Method

Bacteria were applied to plates as disclosed above for EXAMPLE 10 and plates were irrigated and incubated for 30 minutes in water or saline solutions to reduce adhesiveness of colonies. Subsequently, the media in the plates were rinsed by saline fluids to test colonies mobilization; see FIG. 14. The results were as follows:

| Fluid used | % of colonies mobilized | problems |
|---|---|---|
| Sterile water | 50% | Rinsing fluid splash to outside. |
| Half normal saline | 70% | Rinsing fluid splash to outside. |
| Normal saline | 70% | Rinsing fluid splash to outside. |

These data show that rinsing, especially with saline solutions, after irrigation and incubation for 30 minutes is another effective method to reduce the adhesiveness of bacterial colonies to the gel. These results lead of design on a type 2 plate cover which comprises a drainage system with a filter which can prevent fluid splashing and remove waste products, such as rinsing solution, but which will retain microbe colonies.

Example 12: Effects of Post Irrigation Rinsing Using a Type 2 Cover

The effect of incorporating a type 2 cover on to the trianguloid wedge-shaped plates was evaluated; see FIG. 14.

| Fluid used | % of colonies mobilized | % of splash |
|---|---|---|
| | 65% | 0% |
| | 75% | 0% |
| | 75% | 0% |

These data show a more effective rinsing is achieved by using a type 2 cover which prevents splashing as shown by FIG. 14. The type 2 cover allowed proper drainage of waste fluids used for rinsing. At the same time colonies were retained because of the presence of the filter. As shown by the table below, while both methods were effective in obtaining colonies at the apex or tip of the plate, the irrigation and washing method was less effective than the irrigation and curettage method

| | Irrigation and curettage | Irrigation and rinsing |
|---|---|---|
| % of colonies collected to triangle tip | 85% | 75% |

Example 13: Comparison of Conventional Methods with the Method Disclosed Herein

The table below provides a general side-by-side comparison of conventional petri-dish agar and Mueller-Hinton agar methods with an embodiment of the CAC-TAT method disclosed herein.

| Comparison table between the current methods and CAC-TAT | | | |
|---|---|---|---|
| Point of comparison | Conventional Petri-dish agar | Conventional Mueller-Hinton agar | CAC-TAT (invention embodiment) |
| Objectives | To obtain a culture of microbes. | To determine antibiotic sensitivity. | Both |
| Duration | 2-7 days | 2-3 days | About 4-12 hours for culture and another 4-12 hours for determining antibiotic sensitivity. For a total of about 8-24 hrs. |

-continued

Comparison table between the current methods and CAC-TAT

| Point of comparison | Conventional Petri-dish agar | Conventional Mueller-Hinton agar | CAC-TAT (invention embodiment) |
|---|---|---|---|
| Speed in meeting clinical demand | Time consuming | Time consuming | Quick, same day results. |
| Risk of contamination | High because the system is open. | High because the system is open. | Safer, as it is a closed system. |
| Risks of infection to staff | High because the system is open. | High because the system is open. | Safer as it is a closed system. |
| Empirical administration of antibiotics while testing is performed | yes | yes | Usually not needed as testing is rapid. |
| Automation | Difficult or not feasible to automate as methods require significant human manipulation. | Difficult or not feasible to automate as methods require significant human manipulation. | May be performed manually or automated. |
| Standardization | Not feasible because of human variability. | Not feasible because of human variability. | Standardization feasible especially for automated methods with calibrated machine components. |
| Cost | cheap | moderate | Cheap, both systems are used in one. |
| Economy | — | — | Reduces costs by giving rapid results. |
| methods comparison | 1-immerse sterile cotton stick in positive broth fluid culture media. 2-apply the immersed cotton stick on the Petri dish agar media. 3--incubate the Petri dish agar at 37° C. for 2-7 days. 4-daily check for the appearance of microbes colonies 5-once the microbe colonies becomes apparent, choose a large colony and use it to produce a microbe suspension of 0.5 McFarland density strength for use in determining the antibiotic sensitivity | 1--obtain a microbes colony when becomes apparent in petri dish, choose a large one and use it to produce microbe suspension of 0.5 McFarland density strength to use it for the antibiotic sensitivity. 2-a swab from the microbe suspension obtained using sterile cotton stick swabs. 3-spread microbe obtained on the cotton stick all over in Mueller-Hinton agar then apply the antibiotic disks or strips. 4--incubate the agar at 37° C. for 2-7 days. 5-daily check for microbial growth and appearance of zone of inhibition. | For colonies culture method: 1- apply 6 drops positive broth culture using needle gage 21 to Area 1 prior to the wide first trench in CAC-TAT agar. 2-mobilize the drop/drops by moving the drop/drops from side to side to spread maximum in area 1. 3-incubate for 4-12 hours at 37° C. Then small bacterial colonies will be visible. 4-irrigate: Inject half normal saline through the injection rubber using syringe and needle, and incubate for 30 minutes to make the colonies less sticky. Then allow the fluid to discard as wastage through drainage system of cover 2. 5-curretage: Curettage all colonies using curate or knife. 6-apply centrifuging using 400-800 RPM for 5-10 minutes to collect all curettage colonies to the tip of the triangle to form single large colony within few hours 7-alternatively: Rinsing can be used to push colonies toward the triangle tip instead of curettage method but it is less effective. |

| | Comparison table between the current methods and CAC-TAT | | |
|---|---|---|---|
| Point of comparison | Conventional Petri-dish agar | Conventional Mueller-Hinton agar | CAC-TAT (invention embodiment) |
| | | | For Antibiotic sensitivity method: 1--obtain microbe colony when it becomes apparent from previous method or even from petri dish, choose a large one and use it to produce microbe suspension of 0.5 McFarland density strength to use it for the antibiotic sensitivity 2-apply 6 drops using 21 gauge needle from the prepared microbe suspension to area 1. 3-spread the drops to Area 1 as before. 4-centrifuge at 400-800 RPM for 5-10 minutes to allow for graduated spread of the suspension to all areas and passing through all trenches. 5-apply the antibiotic strip to the last 2 or 3 areas then incubate for 4-12 hours. 6-Observe the zone of inhibition of microbial growth around the antibiotic strip within few hours and not days. |

Terminology. Terminology used herein is for the purpose of describing particular embodiments only and is not intended to be limiting of the invention.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A trianguloid culture and centrifuge system, comprising:
   at least one plate having an apical tip and a broader basal end, and
   at least one cover for the plate(s),
   wherein said plate comprises:
      a bottom surface substantially having a shape of an isosceles triangle having an apex at one end and a base comprising the other two points of the triangle at the other end, and
      walls around, and substantially perpendicular to, the bottom surface defining an enclosed trianguloid compartment suitable for containing a non-liquid medium;
   wherein said cover fits over or in the enclosed trianguloid compartment to form a sealed trianguloid space, and further wherein the cover comprises an injectable septum proximal to the basal end of the plate; and
   wherein the cover further comprises a blades applicator for producing concentric trenches on the surface of a non-liquid medium contained in the plate.

2. The trianguloid culturing and centrifuging system of claim 1, wherein the plate and the cover are formed from at least one thermoplastic resin selected from the group consisting of acrylic resin, polylactide resin, polyglycolic acid resin, styrene resin, acrylic-styrene copolymer (MS resin), polycarbonate resin, polyester resin, polyvinyl alcohol resin, ethylene-vinyl alcohol copolymer, thermoplastic elastomer, vinyl chloride resin, and silicone resin.

3. The trianguloid culturing and centrifuging system of claim 1, wherein the basal end of the plate comprises a convex arc and wherein the system substantially has the shape of a segment, sector, or pie-slice of a circle.

4. The trianguloid culturing and centrifuging system of claim 1, wherein the angle at the apical tip ranges from 15 to 90 degrees.

5. The trianguloid culturing and centrifuging system of claim 1, wherein the plate has a length measured from its apical tip to a midpoint of its base ranging from 10 to 20 cm, and a width at its basal end ranging from 5 to 30 cm, wherein the walls have a height ranging from 1 to 3 cm.

6. The trianguloid culturing and centrifuging system of claim 1, wherein the bottom surface of the plate further comprises anchors or ridges which extend from the bottom surface into the trianguloid compartment and which are substantially perpendicular to the bottom surface; wherein the height of the anchors or ridges ranges from about 30 to 50% of the height of the walls of the plate.

7. The trianguloid culturing and centrifuging system of claim 6, wherein said trianguloid compartment in the plate further comprises a non-liquid medium which covers the bottom surface of the plate to a height of no more than 80% of the wall height and to a height of at least 30% of the height of the walls of the plate above the height of the anchors or ridges.

8. The trianguloid culturing and centrifuging system of claim 1, wherein the cover is configured to be secured to the plate.

9. The trianguloid culturing and centrifuging system of claim 1, wherein the cover further comprises at least one clip on each lateral or non-basal side configured to securing to the plate.

10. The trianguloid culturing and centrifuging system of claim 1, wherein the apical tip further comprises an opening that has a filter through which a washing liquid can pass but which retains detached microbial colonies, thereby accumulating and concentrating microbial colonies at the apical tip.

11. The trianguloid culturing and centrifuging system of claim 1, wherein said trianguloid compartment in the plate further comprises a non-liquid medium which covers the bottom surface of the plate to a height of no more than 80% of the wall height.

12. The trianguloid culturing and centrifuging system of claim 11, wherein the non-liquid medium comprises at least one concentric trench between equilateral positions on the lateral side walls of the plate which trench demarks at least one distal concentric area (to the apical tip) and one proximal concentric area on the surface of the non-liquid medium.

13. The trianguloid culturing and centrifuging system of claim 11, wherein the non-liquid medium comprises 4 to 6 concentric trenches between equilateral positions on the side walls of the plate which trenches demark 5 to 7 separate concentric areas on the surface of the non-liquid medium.

14. The trianguloid culturing and centrifuging system of claim 13, wherein a first trench which is most distal from the apical tip is about 3-5 mm wide and about 0.8 to 1.2 mm deep and the other 3 to 5 trenches are about 0.8 to 1.2 mm wide and deep.

15. The trianguloid culturing and centrifuging system of claim 13, wherein the concentric trenches are spaced at approximately equal distances from each other along the distance between the apical tip and a midpoint of the base of the trianguloid plate.

16. A kit comprising the trianguloid culturing and centrifuging system of claim 11, and at least one of a sample containing a microorganism in suspension, a syringe suitable for applying the sample of the microorganism to the non-liquid medium in the plate, a centrifuge configured to rotate the plate with its apical point oriented outward from the axis of rotation of the centrifuge, and an adaptor to securely fit the trianguloid culturing and centrifuging system into a centrifuge and orient the apical tips of the plates outward from an axis of centrifugation.

17. An adaptor system comprising the trianguloid culturing and centrifuging system of claim 1 and an adaptor to securely fit the trianguloid culturing and centrifuging system of claim 1 into a centrifuge so as to keep the system substantially flat with respect to the ground and so as to orient the apical tip of the system outward at a 90 degree angle from the axis of rotation of the centrifuge rotor, wherein said adaptor comprises a plate or other holder that securely clips or otherwise attaches to the exterior bottom of the system, said plate being attached to a hinge which attaches to the centrifuge rotor and which is adjustable so as to keep the system flat during centrifugation, said hinge being optionally attached to the centrifuge rotor via blank centrifuge tube which fits into a tube holder or tube case of a centrifuge.

\* \* \* \* \*